United States Patent
Stickney et al.

(10) Patent No.: US 9,282,911 B2
(45) Date of Patent: Mar. 15, 2016

(54) LINEAR DISPLAY OF ECG SIGNALS

(71) Applicant: Physio-Control, Inc., Redmond, WA (US)

(72) Inventors: Ronald Eugene Stickney, Edmonds, WA (US); Blaine Krusor, Seattle, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

(21) Appl. No.: 13/686,145

(22) Filed: Nov. 27, 2012

(65) Prior Publication Data
US 2014/0148718 A1    May 29, 2014

(51) Int. Cl.
| | | |
|---|---|---|
| *A61B 5/044* | (2006.01) | |
| *A61B 5/04* | (2006.01) | |
| *A61B 5/00* | (2006.01) | |
| *A61N 1/362* | (2006.01) | |
| *A61N 1/365* | (2006.01) | |
| *A61B 5/0452* | (2006.01) | |

(Continued)

(52) U.S. Cl.
CPC ............. *A61B 5/044* (2013.01); *A61B 5/04012* (2013.01); *A61B 5/4836* (2013.01); *A61N 1/3621* (2013.01); *A61N 1/36592* (2013.01); *A61B 5/046* (2013.01); *A61B 5/0424* (2013.01); *A61B 5/0452* (2013.01); *A61B 5/746* (2013.01)

(58) Field of Classification Search
CPC .. A61B 5/0402; A61B 5/04012; A61B 5/044; A61B 5/0452; A61B 5/0468; A61B 5/742; A61B 5/743; A61B 5/746; A61B 5/7275
USPC .................. 600/509, 512, 513, 516, 523–525
See application file for complete search history.

(56) References Cited

U.S. PATENT DOCUMENTS 3,983,867 A * 10/1976 Case .............................. 600/522
6,370,428 B1   4/2002 Snyder et al.
(Continued)

FOREIGN PATENT DOCUMENTS

| EP | 0801959 A2 | 10/1997 |
|---|---|---|
| EP | 0923961 A1 | 6/1999 |
| WO | 2013056194 A1 | 4/2013 |

OTHER PUBLICATIONS

Kligfield P, et al. Recommendations for the Standardization and Interpretation of the Electrocardiogram. J Am Coll Cardiol. 2007;49(10):1109-1127.*

(Continued)

*Primary Examiner* — Eugene Wu
(74) *Attorney, Agent, or Firm* — The Juhasz Law Firm PC

(57) ABSTRACT

An illustrative method and system for displaying ECG data of a patient includes the steps of: receiving an ECG waveform of a patient, determining at least a first attribute of the ECG waveform, and determining at least one data point from the first attribute of the ECG waveform. The first data point and associated first attribute of the ECG waveform are displayed on a linear scale. In an alternative method, the at least one data point is structured in a database of ECG data according to the Cabrera sequence; the display domain of the display is divided into several recurrent display slots; and a sequential one of the several recurrent display slots is associated with the at least one data point, which is displayed on the linear scale in the order in which the at least one data point appears in the Cabrera structured database of ECG data.

25 Claims, 17 Drawing Sheets

(51) Int. Cl.
    *A61B 5/046* (2006.01)
    *A61B 5/0424* (2006.01)

(56) References Cited

U.S. PATENT DOCUMENTS

| | | | |
|---|---|---|---|
| 7,006,865 | B1 | 2/2006 | Cohen et al. |
| 7,925,337 | B2 | 4/2011 | Rajagopalan et al. |
| 8,040,246 | B2 | 10/2011 | Graves et al. |
| 8,054,177 | B2 | 11/2011 | Graves et al. |
| 8,060,193 | B2 | 11/2011 | Rajagopalan et al. |
| 8,154,246 | B1 | 4/2012 | Heitmann |
| 2001/0041920 | A1 | 11/2001 | Starkweather et al. |
| 2003/0097160 | A1 | 5/2003 | Caby et al. |
| 2003/0167074 | A1 | 9/2003 | Merry |
| 2003/0176802 | A1* | 9/2003 | Galen et al. .................. 600/523 |
| 2005/0240112 | A1* | 10/2005 | Fang et al. ................... 600/509 |
| 2005/0261599 | A1* | 11/2005 | Shvilkin et al. .............. 600/515 |
| 2006/0149321 | A1 | 7/2006 | Merry et al. |
| 2006/0149323 | A1 | 7/2006 | Merry et al. |
| 2006/0173498 | A1 | 8/2006 | Banville |
| 2009/0192400 | A1* | 7/2009 | Kamataki ..................... 600/523 |
| 2009/0222539 | A1* | 9/2009 | Lewis et al. .................. 709/221 |
| 2009/0264948 | A1 | 10/2009 | Tamura et al. |
| 2009/0295326 | A1 | 12/2009 | Daynes et al. |
| 2010/0049067 | A1* | 2/2010 | Paine et al. .................. 600/509 |
| 2010/0114236 | A1 | 5/2010 | Jiang et al. |
| 2010/0210961 | A1* | 8/2010 | Rajagopalan et al. ........ 600/523 |
| 2011/0060234 | A1* | 3/2011 | Zhou et al. ................... 600/509 |
| 2011/0160606 | A1 | 6/2011 | Rajagopalan et al. |
| 2011/0184692 | A1* | 7/2011 | Andersen ..................... 702/155 |
| 2011/0208259 | A1 | 8/2011 | Pearce et al. |
| 2012/0041328 | A1 | 2/2012 | Rajagopalan et al. |
| 2012/0323133 | A1* | 12/2012 | Lindauer et al. ............. 600/523 |
| 2013/0096649 | A1 | 4/2013 | Martin et al. |
| 2014/0163395 | A1* | 6/2014 | Sapp et al. ................... 600/483 |

OTHER PUBLICATIONS

Ulrika S. Pahlma et al. Comparison of teaching the basic electrocardiographic concept of frontal plane QRS axis using the classical versus the orderly electrocardiogram limb lead displays, American Heart Journal, vol. 134, Issue 6, Dec. 1997, pp. 1014-1018.*

Stanley T. Andersen et al. Panoramic display of the orderly sequenced 12-lead ECG, Journal of Electrocardiology, vol. 27, Issue 4, Oct. 1994, pp. 347-352.*

Int'l Search Report and Written Opinion, PCT/US2012/071436, mailed Apr. 10, 2013, 13 pages.

Int'l Search Report and Written Opinion, PCT/US2012/071448, mailed Feb. 8, 2013, 11 pages.

Int'l Search Report and Written Opinion, PCT/US2012/071450, mailed May 24, 2013, 10 pages.

Int'l Search Report and Written Opinion, PCT/US2012/071461, mailed Apr. 10, 2013, 14 pages.

O'Connor RE et al. Part 10: acute coronary syndromes: 2010 American Heart Association Guidelines for Cardiopulmonary Resuscitation and Emergency Cardiovascular Care. Circulation. 2010;122 (Supp) 3):S787-817 (32 pages).

Andersen MP, Terkelsen CJ, Struijk JJ. The ST Compass: Spatial visualization of ST-segment deviations and estimation of the ST injury vector. J Electrocardiol. 2009;42:181-9 (9 pages).

Andersen MP, Terkelsen CJ, Sørensen JT, Struijk JJ. Performance of an ST dipole model for description of ST deviations in myocardial ischemia. J Electrocardiol. 2009;42:462-8 (7 pages).

Andersen MP, Terkelsen CJ, Sørensen JT, Kaltoft AK, Nielsen SS, Struijk JJ, Bøtker HE. The ST injury vector: electrocardiogram-based estimation of location and extent of myocardial ischemia. J Electrocardiol. 2010;43:121-31 (11 pages).

Philips Medical Systems. Philips DXL ECG Algorithm Physician's Guide, ed. 3. Andover, MA: Philips Medical Systems; 2009: 3-15-17 (221 pages).

Selvester RH, Wagner GS, Ideker RE. Myocardial infarction. In: Macfarlane PW, Veitch Lawrie TD, eds. Comprehensive Electrocardiology. New York: Permagon Press; 1989: 565-629 (69 pages).

* cited by examiner

DEFIBRILLATION SCENE

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |

TWO MAIN TYPES OF
EXTERNAL DEFIBRILLATORS

FIG. 2

COMPONENTS OF EXTERNAL DEFIBRILLATOR

Small to moderate acute ST vector

Large acute ST vector

| Waveform Order | ECG Lead Order (12 ECG Lead System) | Recurrent Display Slot Order |
|---|---|---|
| 1 | I | 1 (1) |
| 2 | II | 1 (2) |
| 3 | III | 1 (3) |
| 4 | aVR | 2 (1) |
| 5 | aVL | 2 (2) |
| 6 | aVF | 2 (3) |
| 7 | V1 | 3 (1) |
| 8 | V2 | 3 (2) |
| 9 | V3 | 3 (3) |
| 10 | V4 | 4 (1) |
| 11 | V5 | 4 (2) |
| 12 | V6 | 4 (3) |

FIG. 7B
(PRIOR ART)

| Data Order | ECG Lead Order (12 ECG Lead System) | Cabrera Structured ST-Segment Data Set | Recurrent Display Slot Order | Band of Normal Limits | Labels | Anatomical Area |
|---|---|---|---|---|---|---|
| 1 | I | aVL | 855 | $B_{aVL}$ | $L_{aVL}$ | Lateral |
| 2 | II | I | 856 | $B_I$ | $L_I$ | Inferior |
| 3 | III | -aVR | 857 | $B_{-aVR}$ | $L_{-aVR}$ | Inferior |
| 4 | aVR | II | 858 | $B_{II}$ | $L_{II}$ | — |
| 5 | aVL | aVF | 859 | $B_{aVF}$ | $L_{aVF}$ | Lateral |
| 6 | aVF | III | 860 | $B_{III}$ | $L_{III}$ | Inferior |
| 7 | V1 | V1 | 861 | $B_{V1}$ | $L_{V1}$ | Septal/Posterior |
| 8 | V2 | V2 | 862 | $B_{V2}$ | $L_{V2}$ | Septal/Posterior |
| 9 | V3 | V3 | 863 | $B_{V3}$ | $L_{V3}$ | Anterior/Posterior |
| 10 | V4 | V4 | 864 | $B_{V4}$ | $L_{V4}$ | Anterior/Posterior |
| 11 | V5 | V5 | 865 | $B_{V5}$ | $L_{V5}$ | Lateral |
| 12 | V6 | V6 | 866 | $B_{V6}$ | $L_{V6}$ | Lateral |

FIG. 8C

LINEAR DISPLAY OF ECG SIGNALS

The present application claims the benefit of the following provisional application: Prov. Appl. 61/642,401, filed May 3, 2012.

FIELD

This invention generally relates to external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body and from where it returns to the right atrium to start the oxygenation-deoxygenation cycle of the blood all over again.

The heart chambers pump because of the heart's electrical control system. More particularly, the sinoatrial (SA) node generates an electrical impulse, which generates further electrical signals. These further signals cause the above-described contractions of the various chambers in the heart to occur in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In an SCA, the heart fails to pump blood effectively, and, if not corrected, can result in death. It is estimated that SCA results in more than 250,000 deaths per year in the United States alone. Further, an SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not corrected in time, will result in death, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume normal contractions in pumping blood. If VF is not terminated, the shock may be repeated, often at escalating energies.

A challenge with defibrillation is that the electrical shock must be administered very soon after the onset of VF. There is not much time to do this since the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because the blood flow has stopped. They should receive therapy quickly after the onset of VF or they will die.

For a VF victim without an ICD, a different type of defibrillator can be used, which is called an external defibrillator. External defibrillators have been made portable, so they can be brought to a potential VF victim quickly enough to revive them.

During VF, the person's condition deteriorates because the blood is not flowing to the brain, heart, lungs, and other organs. The blood flow must be restored, if resuscitation attempts are to be successful.

Cardiopulmonary Resuscitation (CPR) is one method of forcing blood to again flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows down the deterioration that would otherwise occur while a defibrillator is being retrieved. For patients with an extended down-time, survival rates are higher if CPR is administered prior to defibrillation.

One common challenge for both automated and manual rhythm assessment in connection with defibrillation is to accurately triage patients with chest pain or other symptoms suggestive of a possible acute coronary syndrome (ACS, i.e., acute myocardial ischemia or infarction [AMI]). Although there are many ways of classifying a patient based on ECG waveforms, one particularly effective way is by use of a set of data within the ECG waveform known as an ST-segment. Using the ST-segment of an ECG waveform that may typically be taken from a standard 12-lead ECG, a possible ACS patient may be classified into one of three groups:

1. STEMI (ST elevation myocardial ischemia/infarction)
2. High-risk UA/NSTEMI (unstable angina/non-ST-elevation myocardial ischemia/infarction)
3. Other (either low/intermediate risk UA/NSTEMI, or non-ACS)

The classification of a patient based on ST-segment or other data from an ECG waveform can affect the patient's destination (e.g., catheterization laboratory [cath lab]) and treatment (e.g., prehospital drug therapy).

Accurate triage of possible ACS patients from the 12-lead ECG is a challenge for expert cardiologists and a greater challenge for less-experienced clinicians (e.g., new cardiologists, new emergency physicians, and paramedics). Interpreting the 12-lead ECG for possible ACS patients is challenging for two general reasons. First, there are many patterns of abnormal ST levels that can occur, depending on the patient's coronary anatomy and on where the clot is located in the coronary tree. Second, there are many non-ACS conditions that can cause abnormal ST levels (e.g., left ventricular hypertrophy) or other data readings on an ECG waveform. In addition, automated 12-lead programs cannot achieve the accuracy of expert cardiologists because the triage decision often depends on patient symptoms (e.g., "It feels like an elephant is stepping on my chest"), clinical history (e.g., prior myocardial infarction), and presentation (e.g., chest trauma from a seat belt due to a motor vehicle collision).

Incorrect triage can have substantial consequences. For example, missing a STEMI can result in a large myocardial infarction or even death in a patient whose myocardium could have been salvaged with timely treatment in the cath lab. A false STEMI alert can needlessly bring the cath lab to the hospital in the middle of the night. Missing or mis-reading other data in the waveform of an ECG may also lead to false diagnosis and improper treatment.

While advanced medical device solutions exist for interpreting data in a 12-lead ECG waveform, defibrillator operators may benefit from the display of 12-lead ECG waveforms that are more informative, intuitive and user friendly.

BRIEF SUMMARY

The present description gives instances of devices, systems, software and methods, the use of which may help overcome problems and limitations of the prior art.

An illustrative method for displaying ECG data of a patient includes the steps of: (a) receiving a plurality of ECG waveforms of a patient; (b) determining at least a first attribute of a first ECG waveform of the plurality of the ECG waveforms; (c) determining at least a first data point from the first attribute of the first ECG waveform of the plurality of the ECG waveforms; (d) associating the first attribute of the first ECG waveform to the first data point of the first ECG waveform; (e) repeating steps b through d for a second ECG waveform of the plurality of the ECG waveforms; (f) providing a linear scale on a display; and (g) displaying the first data point and associated first attribute of each of the first ECG waveform and the second ECG waveform on the linear scale.

An alternative method for displaying ECG data of a patient includes the steps of: receiving an ECG waveform of a patient; determining at least one data point from the ECG waveform; structuring the data in a database of ECG data according to the Cabrera sequence; providing a linear scale on a display; dividing a display domain of the display into several recurrent display slots; associating a sequential one of the several recurrent display slots with the at least one data point; displaying the at least one data point on the linear scale in the order in which the at least one data point appears in the Cabrera structured database of ECG data.

An alternative method for displaying ECG data of a patient includes the steps of: determining a data point from ECG data for each ECG lead of a set of ECG leads adapted for monitoring the ECG of a patient to form a data set; structuring the data set according to a predetermined sequence to form a structured data set; dividing a display domain into several recurrent display slots; associating a sequential one of the several recurrent display slots with each data in accordance with the sequential ordering of the each data in the structured data set to form a sequentially display domain ordered structured data set; displaying each data in the sequentially display domain ordered structured data set on a linear scale of the display in the order in which the data appears in the sequentially display domain ordered structured data set.

An ECG monitoring system for identifying ECG deviation data of a patient includes: a set of ECG leads adapted for monitoring the ECG of a patient; a display; and a processor configured to control the display and to execute an instance for identifying ECG deviation of a patient. The instance is configured for: determining a data from ECG data for each ECG lead of the set of ECG leads adapted for monitoring the ECG of a patient to form a data set; structuring the data set according to the Cabrera sequence to form a Cabrera structured data set; dividing a display domain into several recurrent display slots; associating a sequential one of the several recurrent display slots with each data in accordance with the sequential ordering of the each data in the Cabrera structured data set to form a sequentially display domain ordered Cabrera structured data set; displaying each data in the sequentially display domain ordered Cabrera structured data set on a linear scale of a display in the order in which the data appears in the sequentially display domain ordered Cabrera structured data set.

These and other features and advantages of this description will become more readily apparent from the following Detailed Description, which proceeds with reference to the drawings, in which:

BRIEF DESCRIPTION OF THE DRAWINGS

FIG. 2 is a table listing two illustrative types of the external defibrillator shown in FIG. 1B, and who they might be used by.

FIG. 7B shows a prior art table illustrating data for 12 ECG leads and the conventional recurrent display slot order for displaying this 12 ECG lead data on a display.

FIG. 8C shows a table illustrating data for 12 ECG leads and the recurrent display slot order for displaying this 12 ECG lead data on a display according to this disclosure.

DETAILED DESCRIPTION

Figure 1A:
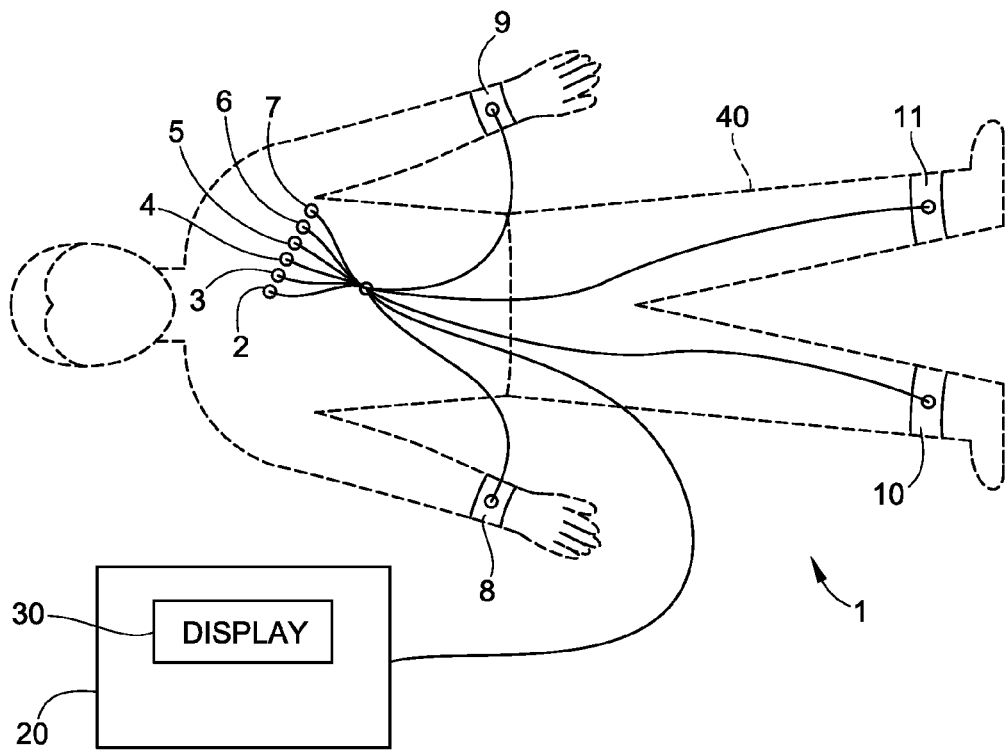
FIGS. 1A and 1B are illustrative diagrams of a scene showing ECG monitoring of a patient and in FIG. 1B also the use of an external defibrillator to provide emergency cardiac patient care, with which this disclosure may be used.
Figure 1B:
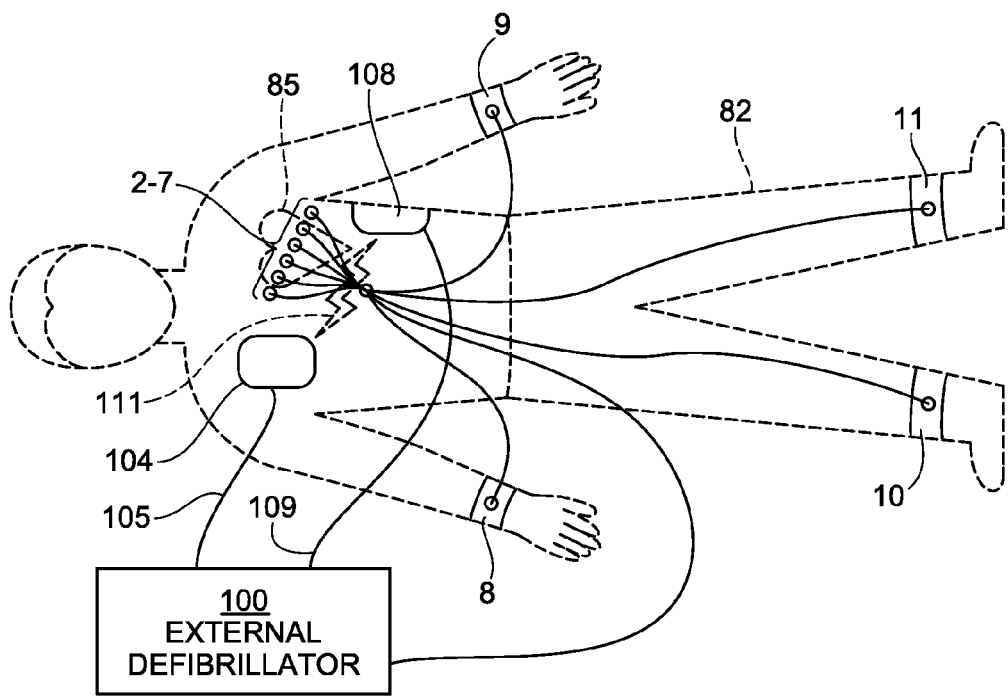

FIGS. 1A and 1B are diagrams of a defibrillation scene showing the use of an external defibrillator to save the life of a person according to this disclosure. As shown in FIG. 1A, a person 82 is lying on his back. Person 82 could be a patient in a hospital, or someone found unconscious, and then turned over onto his back. Person 82 is experiencing a condition in their heart 85, which could be Ventricular Fibrillation (VF).

In FIG. 1B, a portable external defibrillator 100 has been brought close to person 82. At least two defibrillation electrodes 104, 108 are typically provided with external defibrillator 100, and are sometimes called electrodes 104, 108. Electrodes 104, 108 are coupled together with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, also goes through heart 85, in an attempt to restart it, for saving the life of person 82.

Defibrillator 100 can be one of different types, each with different sets of features and capabilities. The set of capabilities of defibrillator 100 is determined based upon who would use it and what training they would be likely to have. Examples are now described.

FIG. 2 is a table listing two typical types of external defibrillators, and who they are primarily intended to be used by. A first type of defibrillator 100 is generally called a defibrillator-monitor, because the defibrillator part is typically formed as a single unit with a patient monitor part. A defibrillator-monitor is sometimes called monitor-defibrillator. A defibrillator-monitor is intended to be used by persons in the medical profession, such as doctors, nurses, paramedics, emergency medical technicians, etc. who may be trained to provide medical treatment to the patient during a defibrillation process based upon information provided by the monitor. Such a defibrillator-monitor is intended to be used in a pre-hospital or hospital scenario.

The defibrillator part may be dedicated to a particular mode of operation. Alternatively, the defibrillator part may be configured to operate in more than one modes of operation. One mode of operation of the defibrillator part may be that of an automated defibrillator, which can determine whether a shock is needed and, if so, charge to a predetermined energy level and instruct the user to administer the shock. Another mode of operation may be that of a manual defibrillator, where the user determines the need and controls administering the shock. In this embodiment, one illustrative defibrillator is configured to enable both automated defibrillation and manual defibrillation modes of operation depending upon the selection of the user. As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1B. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not trained in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Often, the people who will first reach the VF sufferer may not be in the medical profession.

Increasing awareness of the short survival time of a patient experiencing a VF, has resulted in AEDs being deployed more pervasively in public or semi-public spaces, enabling members of the public to use one provided they have obtained first aid and CPR/AED training. In this way, defibrillation can be administered sooner after the onset of VF, to hopefully be effective in rescuing the person.

There are additional types of external defibrillators, which are not listed in FIG. 2. For example, a hybrid defibrillator can have aspects of an AED, and also of a defibrillator-monitor. An illustrative example may be an AED provided with an ECG monitoring capability.

Figure 3:
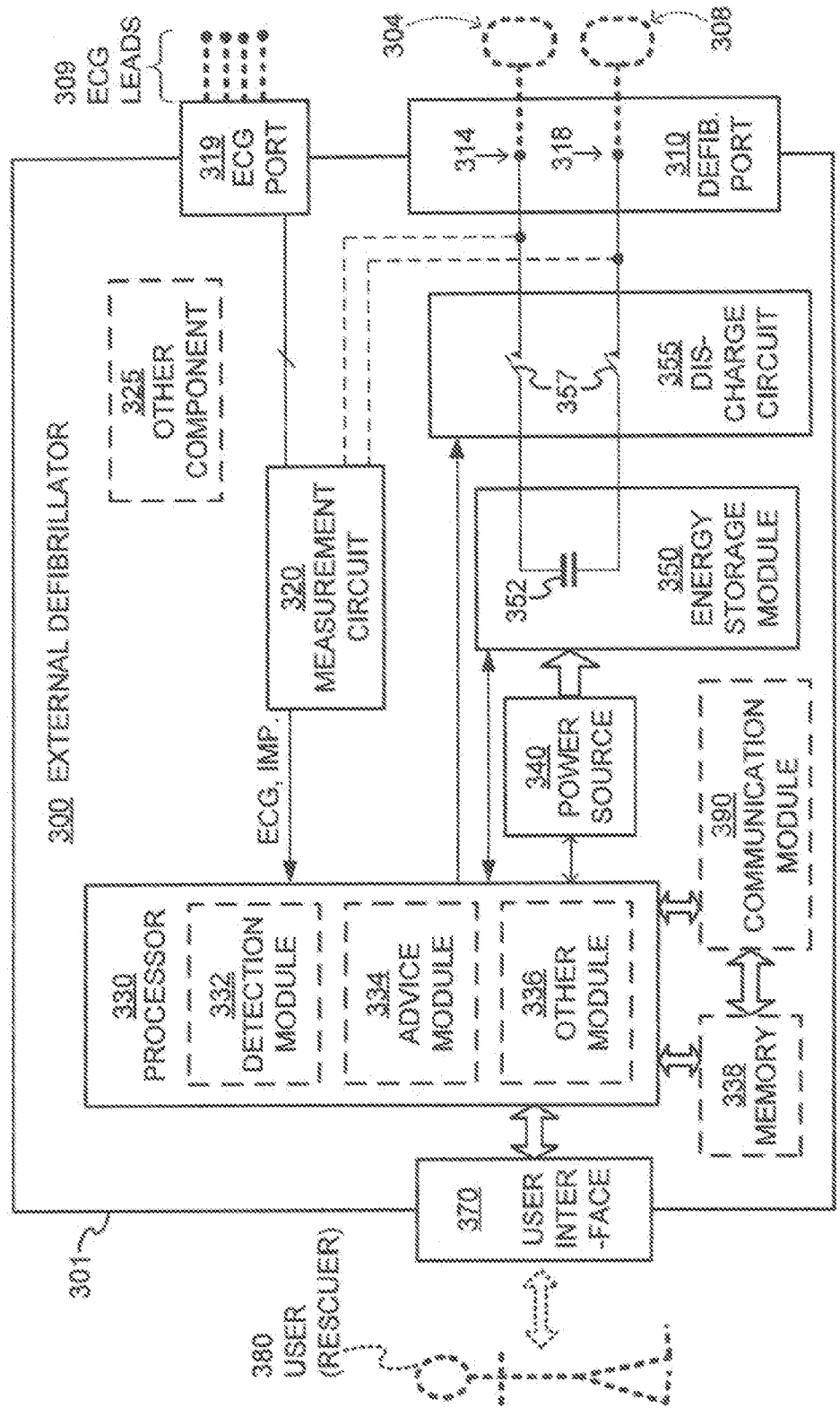
FIG. 3 is a diagram showing components of an external defibrillator, such as the one shown in FIG. 1B, configured in an illustrative embodiment.

FIG. 3 is a diagram showing components of an external defibrillator 300 configured in an illustrative embodiment according to this disclosure. These components can be configured, for example, in external defibrillator 100 of FIG. 1B. Plus, these components of FIG. 3 can be provided in a housing 301, which is also known as casing 301.

External defibrillator 300 is intended for use by a user 380, who would be the rescuer. Defibrillator 300 typically includes a defibrillation port 310, which may be configured as a socket (not shown) in housing 301. Defibrillation port 310 includes nodes 314, 318. Defibrillation electrodes 304, 308, which can be similar to electrodes 104, 108 in FIG. 1B, can be plugged into defibrillation port 310, so as to make electrical contact with nodes 314, 318, respectively. It is also possible that electrodes can be hard-wired to defibrillation port 310, etc. Either way, defibrillation port 310 can be used for guiding to person 82 via electrodes an electrical charge that has been stored in defibrillator 300, as discussed below.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or a signal taken from a different number of leads. Moreover, a defibrillator-monitor could have additional ports (not shown), and another component 325 for the above described additional features, such as for receipt of patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals in this case through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 may include a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at a piece of instructional advice based on outputs of detection module 332. Advice module 334 can include a Shock Advisory Algorithm residing in a memory unit (not shown) in the advice module for instructing the processor to implement decision rules, etc. Alternatively, the Shock Advisory Algorithm may reside in part or in whole on a memory 338 of the defibrillator. The instruction to the processor can be to shock, to not shock, to administer other forms of therapy, and so on. If the instruction to the processor is to shock, in some external defibrillator embodiments, the processor is configured to report that instruction to the user via user interface 370, and to prompt the user to do it. In other embodiments, the processor may be configured to execute the instructional advice, by administering the shock. If the instructional advice is to administer CPR, the processor may be configured to enable defibrillator 300 to issue prompts to administer CPR, etc.

Processor 330 can include additional modules, such as module 336, for other functions. In addition, if other component 325 is provided, it may be operated in part by processor 330 or by another processor.

Defibrillator 300 optionally further includes the memory 338, which can work together with processor 330. Memory 338 may be implemented in any number of ways. Such ways include, by way of example and not of limitation, nonvolatile memories (NVM), read-only memories (ROM), random access memories (RAM), any combination of these, etc. Memory 338, if provided, may include programs containing instructions for execution by processor 330 or other processors that may be included in the external defibrillator. The programs provide instructions for execution by the processor 330, and can also include instructions regarding protocols and decision making analytics, etc. that can be used by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include an AC power override, whereby AC power, instead of power from power source 340 is delivered to an energy storage module 350 when AC power is available. In some embodiments, power source 340 is controlled by processor 330.

Defibrillator 300 additionally includes the energy storage module 350. Module 350 is where electrical energy is stored in preparation for a sudden discharge to administer a shock. The charge to module 350 from power source 340 to the right amount of energy can be controlled by processor 330. In typical implementations, module 350 includes one or more capacitors 352, and may include other circuitry.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and in other ways well known in the art.

Defibrillator 300 further includes the user interface 370 for user 380. User interface 370 can be made in any number of ways. For example, interface 370 may include a screen, to display a parameter of a patient that is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other devices. Such communication can be performed wirelessly, or via wire, or by infrared communication, and so on. In this way, data can be communicated from the defibrillator 300 to external devices, such as patient data, incident information, therapy attempted, CPR performance, and so on.

Electrocardiography is a technique of measuring the bio-electrical currents generated by the heart. These bio-currents can be detected inside the body or at the skin using electrodes. The signals are typically detected using a pair of electrodes placed on the body. The ECG voltage potential between those pairs of electrodes can be measured and recorded. The graphical display of these currents is known as an electrocardiogram, which is often referred to as an ECG. The ECG is useful in revealing the condition of the heart and to diagnosis heart ailments or disease.

Figure 4A:
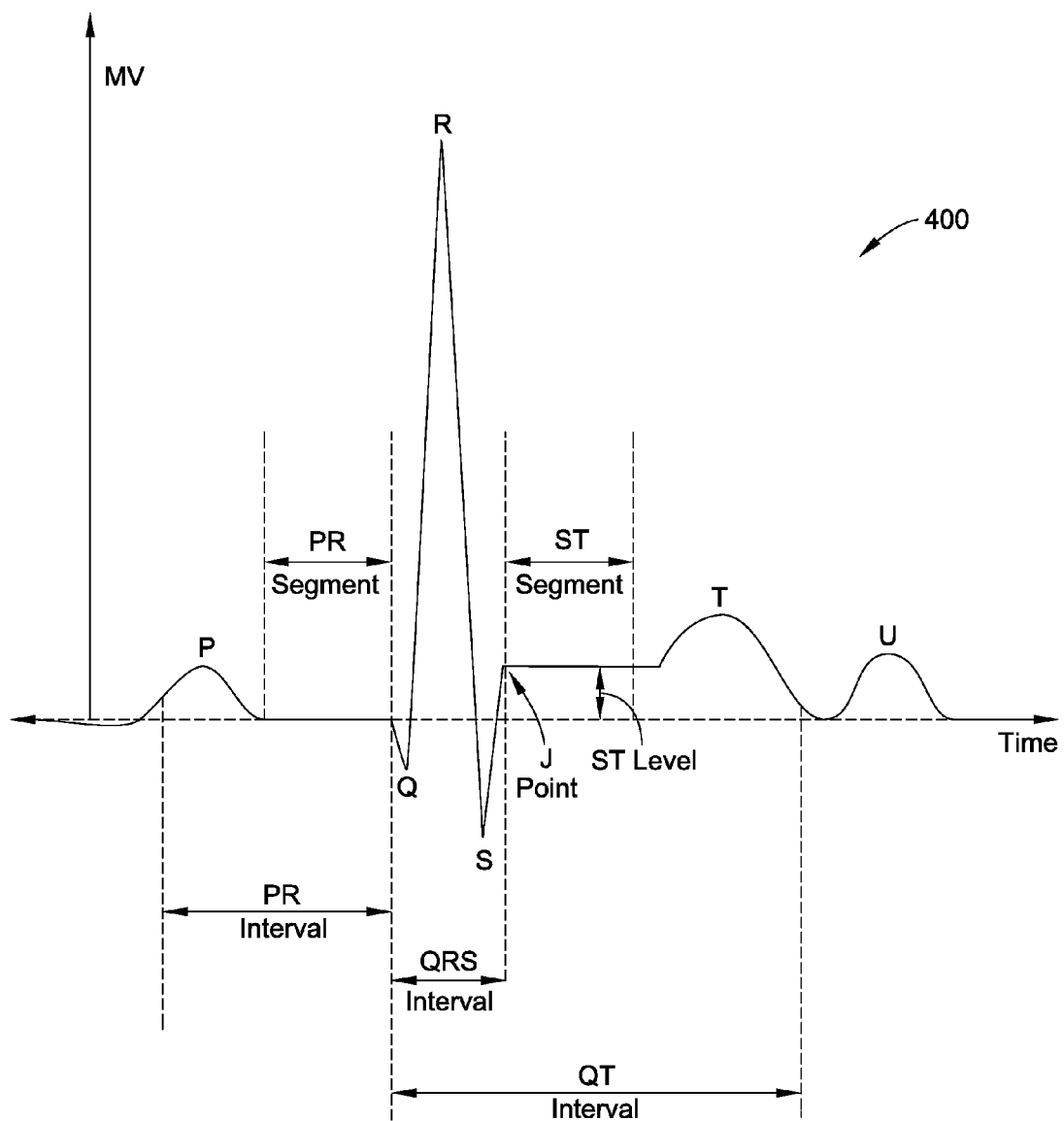
FIG. 4A illustrates an ECG waveform of a patient.

FIG. 4A illustrates a prior art ECG signal 400 taken from electrodes placed on a patient. The ECG includes several data and patterns of data that indicate rhythms of the heart. These data and patterns may vary from patient to patient but for healthy patients these data and patterns have general similarities. Some of these data and patterns include PR interval, PR segment, QRS interval, ST segment, ST interval, etc. patterns, and data related thereto. These and other data and patterns from an ECG indicate various rhythms of the heart and are well known in the art. The data and patterns embodied in an ECG of a healthy patient provide a baseline for a healthy heart of that patient. Deviations in data and patterns from this baseline may indicate heart irregularity, ailment, or disease.

ECG data and patterns from a heart can be defined based upon a number of factors including the number of electrodes that are placed on the human body and where those electrodes are placed. A pair of electrodes is known in the art as an ECG lead. Over the years, a standard has been established in electrocardiography that specifies 10 electrodes placed on a patient configured to define 12 separate leads. Each ECG lead detects the ECG voltage potential between one of a pair of the 10 electrodes that form the ECG lead. The orientation of those ECG leads with respect to the heart also provides a directional component to the ECG voltage detected. The ECG voltage together with its directional component form a vector and the display of vectored ECG voltages provide additional information on both heart rhythm magnitude and angle.

In the standard 12 ECG lead system, the ECG leads are divided into limb leads, called—I, II, III, AVR, AVL and AVF—and chest leads called—V1, V2, V3, V4, V5, V6. The limb leads provide views of the cardiac activity in the frontal plane and the chest leads provide views in the horizontal plane of the heart. Limb lead I is taken between a negative electrode placed on the right arm and a positive electrode placed on the left arm; limb lead II between a negative electrode placed on the right arm and a positive electrode placed on the left foot; and so forth. These and the other electrode pairings to form the 12 ECG lead orientations are well known in heart.

Figure 4B:
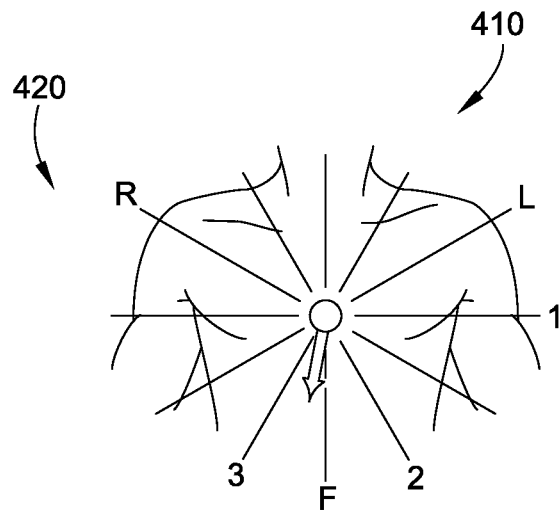
FIGS. 4B-4C illustrate prior art ST vector plots for displaying ST-segment deviations, with inferior STEMI on the left, FIG. 4B, and with anteroseptal STEMI on the right, FIG. 4C.
Figure 4C:
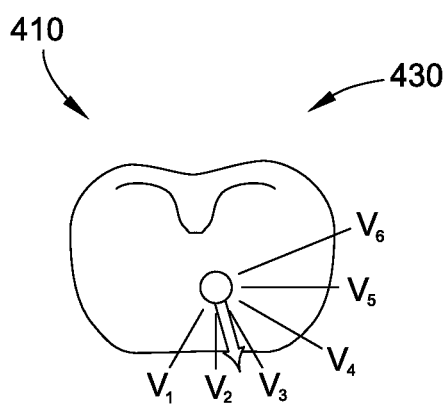

There are many ways in which vectored ECG data may be used to diagnose the rhythms of the heart. One conventional technique employs ST vector plots to diagnose the rhythm of a heartbeat. The plotted ST-segment level may indicate a STEMI (ST elevation myocardial ischemia/infarction), a high-risk UA/NSTEMI (unstable angina/non-ST-elevation myocardial ischemia/infarction); or other condition (either low/intermediate risk UA/NSTEMI, or non-ACS). FIGS. 4B-4C depict two vector plots 410 comprising a first ST vector plot 420, FIG. 4B and a second vector plot 430, FIG. 4C. First vector plot 420 shows how the vectored ST-segment data from the six orientations I, II, III, AVR, AVL and AVF in a standard 12 ECG system may be added together. A resulting vector that is small may indicate a normal heart rhythm. The resulting vector shown in the first vector plot 420 on the other hand indicates a small to moderate acute ST vector. In second vector plot 430 shown in FIG. 4C, the vectored ST-segment data from the six orientations V1, V2, V3, V4, V5, V6 in the standard 12 ECG system are shown added together. A resulting vector that is small may indicate a normal heart rhythm. The resulting vector shown in the second vector plot 430 on the other hand indicates a large acute ST vector.

Figure 5A:
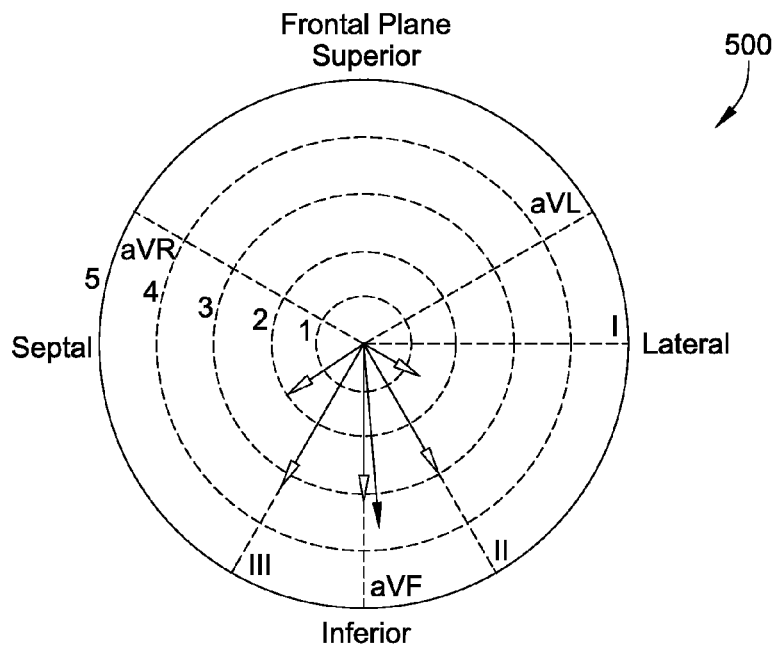
FIG. 5A illustrates a prior art ST Compass for displaying frontal ECG plane ST-segment deviations, and with FIG. 5B displaying a horizontal ECG plane, showing a large inferior STEMI that involves the posterior wall.
Figure 5B:
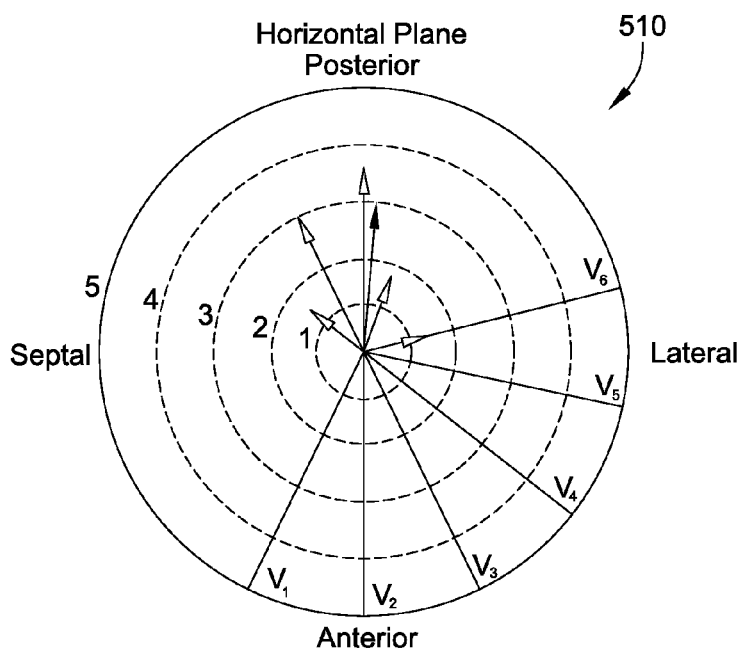

Another conventional technique utilizing ECG data to diagnose the rhythms of the heart employs ST vector plots to create "ST Compass" plots 500, 510 shown in FIGS. 5A-5B. In this technique, ST levels are plotted on two polar plots, a first plot 500 for the frontal ECG plane (limb leads, FIG. 5A) and a second plot, 510 for the horizontal ECG plane (V leads, FIG. 5B). As shown in FIGS. 5A-5B, a hollow arrow plots the ST value for each lead and a solid arrow plots the overall ST vector in both planes. For STEMI patients, the ST vector points approximately to the center of the area at risk and the vector magnitude is somewhat correlated with the size of the area at risk.

Figure 6A:
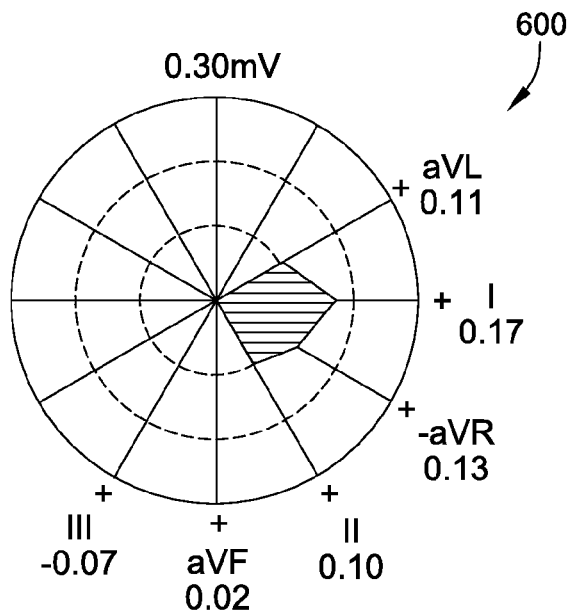
FIGS. 6A-6B illustrate prior art ST Maps, respectively, for the frontal plane and horizontal plane, for displaying ST-segment deviations, showing a large anterior STEMI that includes the septal and lateral walls.
Figure 6B:
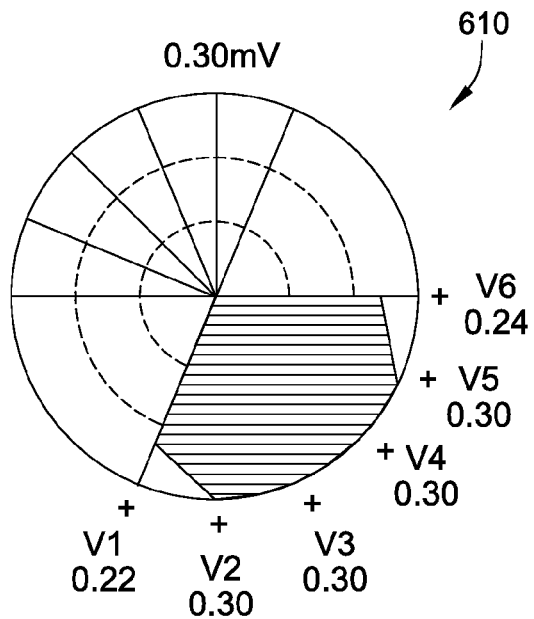

Yet another conventional technique utilizing ECG data to diagnose the rhythms of the heart employs ST vector plots to create "ST Map" plots 600, 610 as shown in FIGS. 6A-6B. In this technique, the ST level for each lead is plotted in the frontal plane 600, FIG. 6A, or horizontal plane 610, FIG. 6B, and the dots are connected to form an area that, for STEMI patients, is somewhat correlated with the location and size of the area at risk.

Figure 7A:
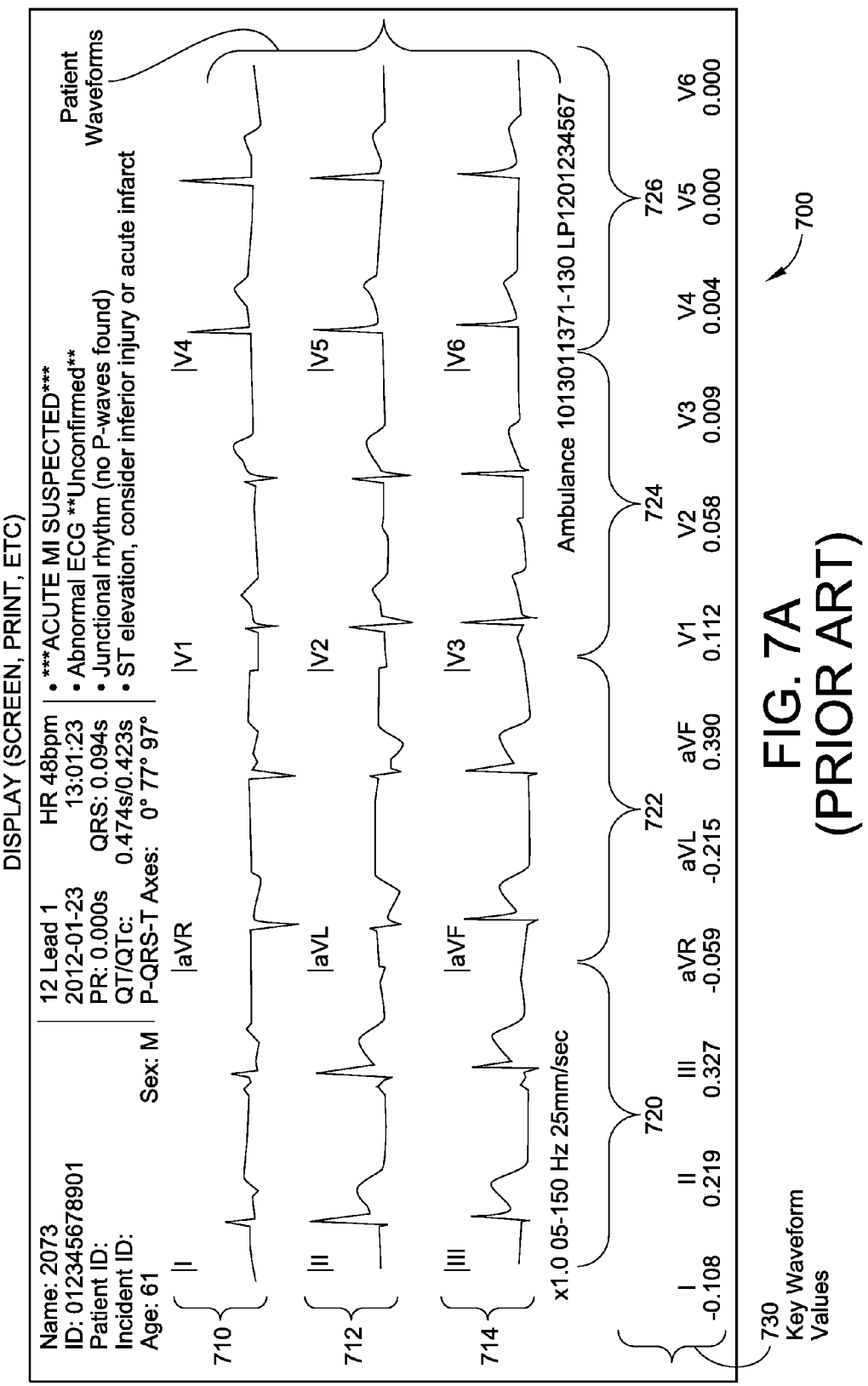
FIG. 7A shows an illustrative prior art ECG signal from a patient with a display of the amplitude of the individual electrode signals that make up the ECG signal based on conventional ordering techniques.

More typically, the data from the 12 ECG leads is displayed in the form of ECG waveforms on an ECG display 700 as shown in prior art FIG. 7A. In conventional displays, the twelve ECG waveforms from the 12 ECG lead system are typically displayed as shown in FIG. 7B in the sequential order shown in the column referred to as ECG lead order 750 for 12 ACG leads. This sequential ordering of the 12 ECG leads is typically as follows: I, II, III, AVR, AVL, AVF, V1, V2, V3, V4, V5, V6. The numerical progression of this sequential ordering is shown in FIG. 7B in the column referred to as waveform order 740 which begins with numbering the waveform generated by ECG lead "I" of the ECG lead order 750 with the waveform order 740 number "1" and ends with numbering the waveform generated by ECG lead "V6" of the ECG lead order 750 with the waveform order 740 number "12."

Because of the limited display space available on display 700 of FIG. 7A, it is generally not possible to meaningfully display all of the ECG waveform data from the 12 ECG leads in the sequence depicted in waveform order 740 (FIG. 7B) on one line of the display. For this reason, the conventional display 700 of FIG. 7A is typically divided illustratively into three display rows 710, 712, and 714 as shown in FIG. 7A, one above each other, and four columns 720, 722, 724, and 726. The display of ECG waveform data in the sequence depicted in waveform order 740 (FIG. 7B) thus occurs by displaying the waveform from ECG leads on display 700 of FIG. 7A as follows: the waveform from ECG leads I, II, and III in column 720 are displayed one above each other in rows 710, 712, and 714, respectively; the waveform from ECG leads aVR, aVL, and aVF in column 722 are displayed one above each other in rows 710, 712, and 714, respectively; the waveform from ECG leads V1, V2, and V3 in column 724 are displayed one above each other in rows 710, 712, and 714, respectively; and the waveforms from ECG leads V4, V5, and V6 in column 724 are displayed one above each other in rows 710, 712, and 714, respectively. To read the ECG waveforms from the 12 ECG leads displayed on the display 700 in the sequence depicted in the waveform order 740 (FIG. 7B), the user needs to read the ECG waveforms first in column 720 going from top row 710 to bottom row 712, then move over one column to column 720 to do the same, and so on.

There are many ways to display the ECG waveforms from the 12 leads on display 700 of FIG. 7A. In one approach, a recurrent display slot order 760 shown in FIG. 7B is associated with each ECG lead appearing in the ECG lead order 750. The recurrent display slot order 760 associates the ECG waveform for each lead listed in the ECG lead order 750 with one of the twelve display spaces or slots in which the display 700 has been divided in this example. In particular, each display space or slot is defined as the space lying at the intersection of one of rows 710, 712, 714 and columns 720, 722, 724, 726. The intersection is shown in FIG. 7B as a numbered pair with the first number representing the column and the second number representing the row of that display space or slot. For example, the recurrent display slot order 760 for the waveform generated by lead I is defined by the number pair 1(1) which indicates that the ECG waveform from lead I will recurrently be displayed in column 1, row 1 on display 700. Similarly, the recurrent display slot 760 for ECG waveform II is 1(2) indicating that the ECG waveform from lead II will recurrently be displayed in column 1, row 2 on the display. In other words, the waveform from ECG lead II will be displayed directly below the waveform from ECG lead I in the first column. The recurrent display slot 760 for the ECG waveform from lead III is 1(3) indicating that the waveform from lead III will recurrently be displayed in column 1, row 3 on the display. Hence, the waveform from ECG lead III will be displayed right below the waveform from ECG lead II in the first column. The next ECG waveform in the display sequence is aVR which cannot be displayed in the first column since there is no more space on the display to do this. Hence, the waveform for ECG lead aVR is shown displayed in column 2, row 1. In this way, the ordered display of the ECG waveforms from the 12 ECG leads (as they appear in the ECG lead order 750 in FIG. 7B) is maintained on the display 700 of FIG. 7A.

The visual effect of the display of the ECG data from different leads in this way is a confluence of a massive amount of data in an order that is difficult to read and interpret. For example, an intuitive read of the display might be reading the waveforms from left to right, the same as reading a sentence. In this read, the user sees ECG waveforms from leads I, aVR, V1, and V4 displayed across row 710, ECG waveforms from leads III, aVL, V2, and V5 displayed across row 712, and ECG waveforms from leads III, aVF, V3, and V6 across row 714. Instead, the waveforms are typically read in the sequential ECG lead order 750 depicted in FIG. 7B. A great deal of training and skill is thus required to read and interpret the ECG waveforms displayed on display 700 of FIG. 7A.

Figure 7C:
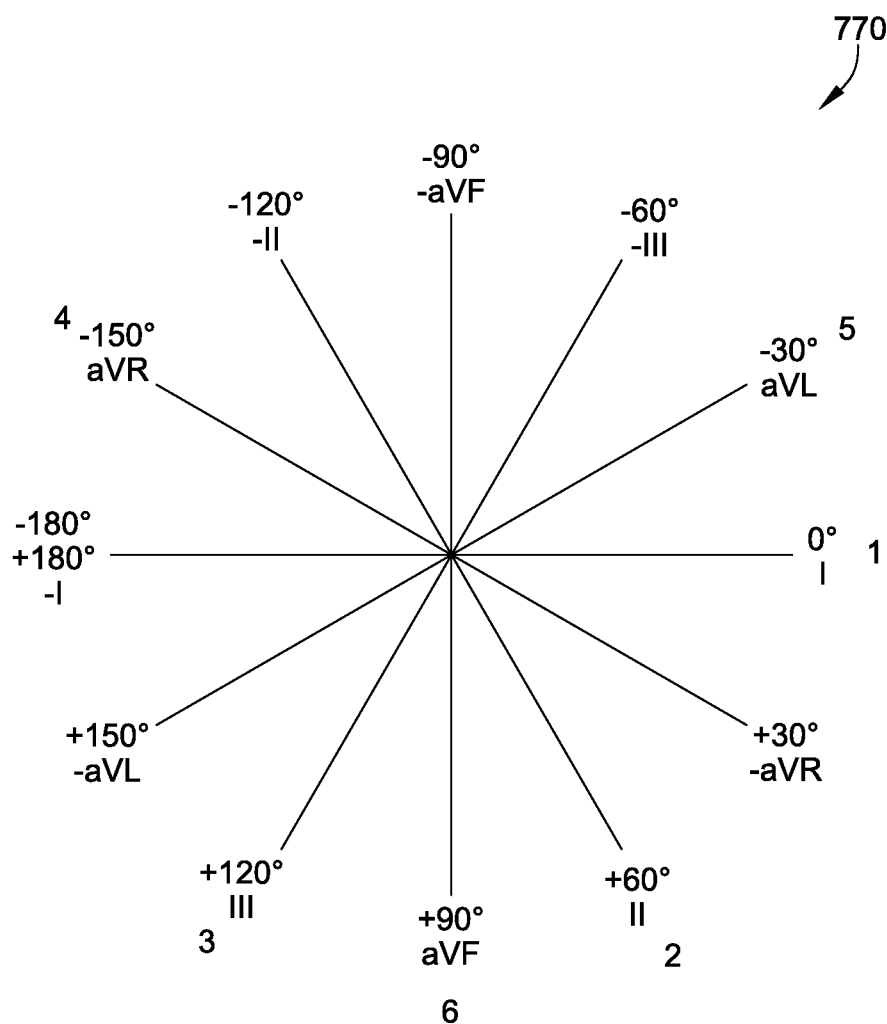
FIG. 7C shows the orientation plane of each lead of a set of electrodes adapted for monitoring an ECG signal and the order in which they are displayed on a conventional display.

Also complicating the intuitiveness of interpreting the ECG waveforms in FIG. 7A and what they mean is that the ECG waveforms displayed on display 700 are displaying time domain information only. Each ECG waveform from each of the 12 ECG leads shows the impedance across that lead as that impedance is changing over time. Hence, the ECG waveform itself does not contain information on the vector orientation of that ECG waveform with respect to the heart. These vector orientations are shown in FIG. 7C which depicts the vector orientation plane 770 of the waveform taken from each of ECG leads I, II, III, aVR, aVL, aVF. As previously discussed, ECG waveforms are displayed on the FIG. 7A display in the sequential order of the ECG lead order 750 (FIG. 7B)— namely, ECG leads I, II, III, aVR, aVL, aVF. These ECG leads are indentified with the numbers 1 to 6 in FIG. 7C. As evident from FIG. 7C, the sequential order in which the waveforms from the ECG leads are displayed (i.e., ECG lead order 750) is entirely different from the sequential order of the orientation planes of those ECG waveforms as shown in FIG. 7C. In particular, as the ECG waveforms are being sequentially displayed in the order I, II, III, aVR, aVL, aVF (according to the ECG lead order 750 in FIG. 7B), the orientation planes of the ECG waveforms from these ECG leads are being displayed in the following order: 1) 0:180 degree plane to the 2) +60:-120 degree plane to the 3) -60:+120 degree plane to the 4) +30:-150 degree plane to the 5) -30:+150 degree plane and finally to the 6) -90:+90 degree plane, before the display of the orientation planes of these ECG waveforms in this same order starts all over again. Hence, in the conventional display shown in FIG. 7A, there is no correlation between the order in which the ECG waveforms from the different ECG leads are displayed (as per the ECG lead order 750 in FIG. 7B) and the order of the orientation planes of those ECG waveforms.

Figure 8A:
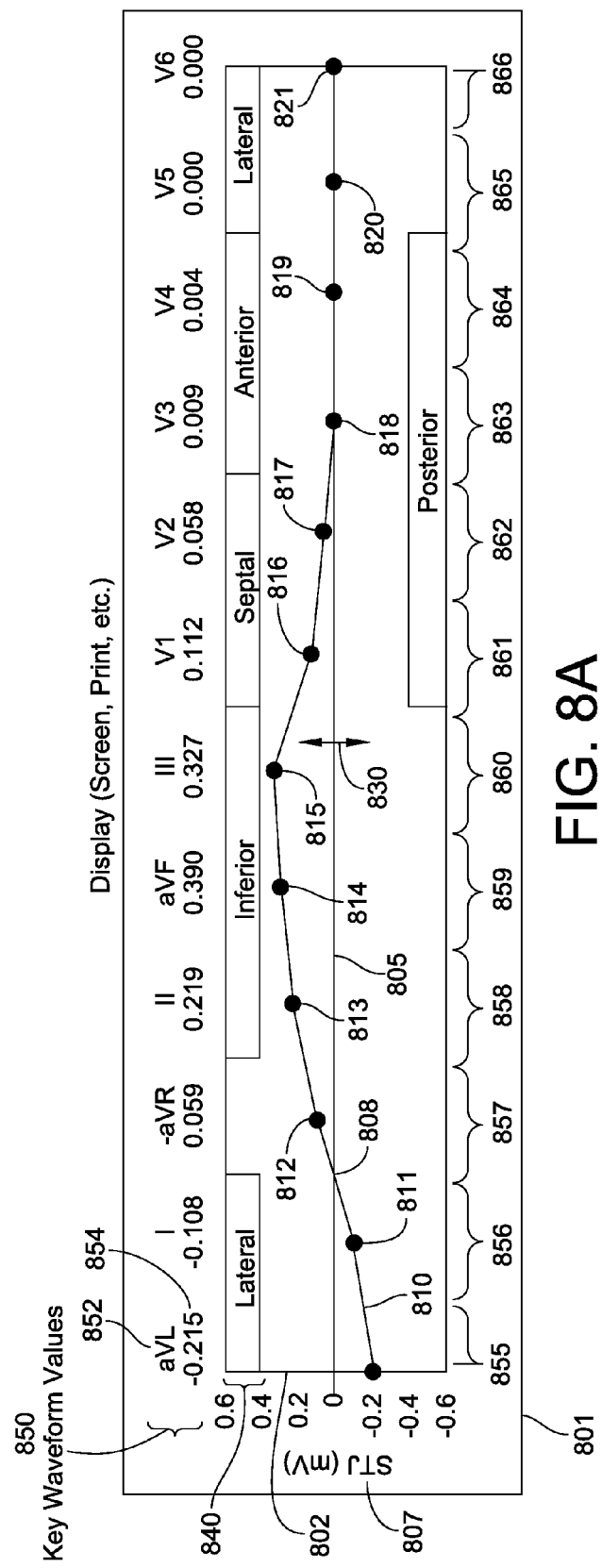
FIG. 8A shows a display of ECG data from a patient according to an illustrative method of this disclosure.

FIG. 8A shows a display 800 of ECG data from a patient according to an illustrative method and system of this disclosure. The display 800 comprises a linear scale 801, an attribute 807, one or more data points 810-821, a waveform 808, a band of normal limits 830, an anatomical area 840, and a display of key waveform values 850.

Attribute 807 is a pattern or data in an ECG waveform. These patterns or data may include patterns such as PR interval, PR segment, QRS interval, ST segment, ST interval, etc. and data pertinent thereto as described in FIG. 4A. Attribute 807 is an indicator of the health of a heart. The attribute 807 of (i.e., patterns and data in an) ECG waveform of a healthy patient provide a baseline for a healthy heart of that patient. Deviations in the attribute (i.e., patterns and data) from this baseline may indicate heart irregularity, ailment, or disease. In the example shown in FIG. 8A, attribute 807 is an ST segment. As previously described, ST-segment data provides one particularly effective way of classifying the heart condition of a patient. Alternatively, any attribute (i.e., pattern or data) in the ECG waveform may be used with this disclosure. The discussion in connection with FIG. 4 above describes some of the other patterns and data which may be used with this disclosure.

The one or more data points 810-821 illustratively represent one or more singular points of data taken from one or more ECG waveforms generated by ECG leads. FIG. 8A shows one or more data points 810-812 comprising 12 singular data points illustratively taken from one of each ECG waveform generated by 12 ECG leads that form the 12 ECG standard. Alternatively, one or more data points 810-812 may be made up of a singular data point, two singular data points, or any number of singular data points. In the example shown in FIG. 8A, each of the 12 data points is associated with the attribute 807 which is ST-segment data in this example. Specifically, the 12 data points represent singular data points taken from an ST-segment attribute of the 12 ECG waveforms that are generated by the 12 ECG leads. While illustratively the attribute is the ST-segment pattern of the ECG waveforms that are generated by the ECG waveforms from the 12 ECG leads, the singular data points may be taken from other attributes of these ECG waveforms. Even more specifically, each of the 12 data points is taken from a different one of the 12 ECG waveforms generated by the 12 ECG leads so that each of the 12 data points represents a singular data point taken from a different one of the 12 ECG waveforms generated by the ECG leads; the attribute being ST-segment data in this example. Hence, the 12 data points 810-821 shown in FIG. 8A form a collection of 12 singular data points, each associated with an attribute of an ECG waveform taken from each of the 12 ECG leads and in the illustrative example each data point represents a value for the ST-segment data found in the ECG waveform generated by the ECG lead. Alternatively, the single data point taken from any one or more of the ECG waveforms may represent an attribute that is other than an ST-segment, such as the attribute derived from the pattern of the ECG waveform known as the PR interval, the PR segment, the QRS interval, the ST segment, the ST interval, or any other pattern or data point of the ECG waveform.

The display of a singular data point that is associated with an attribute of an ECG waveform advantageously provides the user with information on an attribute of an ECG waveform that has been interpreted for the user in a manner described below and presented to the user in the form of a singular data point. The singular data point provides the user with a good ST-segment value to use in his diagnosis. This eliminates the need for the user to have to determine the appropriate ST-segment level to use in his diagnosis based upon the user's interpretation of the set of data that makes up the ST-segment in the ECG waveform, as would be the case when reading conventional ECG waveforms as depicted in FIG. 7A. Hence, the user is able to quickly know what is a good ST-segment level to use for his diagnosis based upon a simple observation of the singular data point that is displayed on the display of this disclosure instead of having to interpret large amounts of data that form the ST-segment pattern in an ECG waveform in order to determine an appropriate ST-segment value on which to base his diagnosis.

The value for the ST-segment found in the ECG waveform generated by the ECG lead is illustratively determined based on an average of the data points that make up the ST-segment. Alternatively, the value for the ST-segment may be a weighted average or determined in other ways. The determination may involve amplitude and level analysis done on the data points that make up the ST-segment. The determination may involve frequency (spectral) analysis; noise and distortion analysis; pulse and transition analysis; time domain analysis. The determination may involve signal processing; digital filtering processing; convolution and correlation processing; frequency domain processing; joint time-frequency analysis signal processing; sampling/resampling processing; signal generation processing; spectral analysis processing; transform processing; time domain processing; and wavelet and filter bank processing.

Waveform 808 is a waveform defined by the interconnection of adjacent data points of the one or more data points 810-821. As previously discussed, each singular data point shown in FIG. 7A provides the user with a point of data representing the value of the ST-segment pattern in an ECG waveform as the value of that ST-segment pattern has been interpreted according to this disclosure. In effect, each singular data point provides the user with a first level or order of interpretation of the ST-segment pattern in an ECG waveform from an ECG lead. Advantageously, waveform 808 transforms this first order interpretation of the ST-segment pattern in an ECG waveform from each ECG lead into a second level or order of interpretation of ST-segment pattern data for the user to use based upon the set of first order interpretations for the entire set of 12 ECG leads in the illustrative example. The displayed set of first order interpretations thus defines an envelope of second order interpretation that advantageously provides the user with further interpretive information on the collection of ST-segment patterns being generated by the constellation of ECG leads. Depending on how that envelope of second order interpretation is changing in time based on the changes over time of the first order interpretive data points making up the envelope, the user may glean valuable information additional to each singular data point about the rhythm of the heart.

The linear scale 801 includes a horizontal axis 805 and a vertical axis 802 for displaying the one or more data points. The horizontal axis 805 and the vertical axis 802 provide an x-y graph or a Cartesian coordinate system for displaying the one or more data on the display 800. Illustratively, horizontal axis 805 represents a sequential ordering of the one or more data points taken from the one or more ECG leads. Vertical axis 802 represents a magnitude for the one or more data points. As previously described, in the illustrative example shown in FIG. 8A, the one or more data points are taken from the attribute of the ECG waveform known as the ST-segment. Hence, each of the one or more data points represents the value or magnitude for the ST-segment found in the ECG waveform generated by the ECG lead as determined in the manner previously described. The magnitude of the ST-segment data captured for display is displayed on the vertical axis 802 illustratively in millivolts (mV). Alternatively, the magnitude may be displayed in different ways such as a value of current, using a different scale, etc.

The display of key waveform values 850 in FIG. 8A includes a sequential ordering position 852 of the one or more data points on the display 800 and a value 854 for each of the one or more data points shown on the display 800. The ordering position 852 and the value 854 for each of the one or more data points are advantageously associated with the one or more data points and the ordering position 852 and the value 854 are displayed on display 800 in a manner that shows this association to the user. An association of each of the one or more data points to the ordering position 852 and the value 854 for the data point and the display of this data in a manner that shows this association to the user brings important information together for the user in a simple, easy to use, intuitive form.

As shown in FIG. 8A, the sequential ordering position 852 of the one or more data points 810-821 taken from the ECG waveforms from the one or more ECG leads is illustratively in the order that those ECG leads appear in the Cabrera sequence. The Cabrera sequence order for ECG leads is aVL, I, -aVR, II, aVF, III, V1, V2, V3, V4, V5, and V6. Alternatively, the one or more data points may be arranged on the display 800 in other sequential orders. As shown in FIG. 8A, the one or more data points on the display 800 includes 12 ST-segment data points, each one data point is taken from a different one of the ECG waveforms generated by the 12 ECG leads, and the 12 ST-segment data points are displayed on display 800 in accordance with the Cabrera sequence. The ordering position 852 and the value 854 for each of the 12 ST-segment data points in their ordered position is illustratively shown as the Cabrera sequence in mV as follows: aVL:-0.215; I:-0.108; -aVR:0.059; 11:0.219; aVF: 0.390; III: 0.327; V1: 0.112; V2:0.058; V3: 0.009; V4: 0.004; V5: 0.000; and V6:0.000.

Figure 8B:
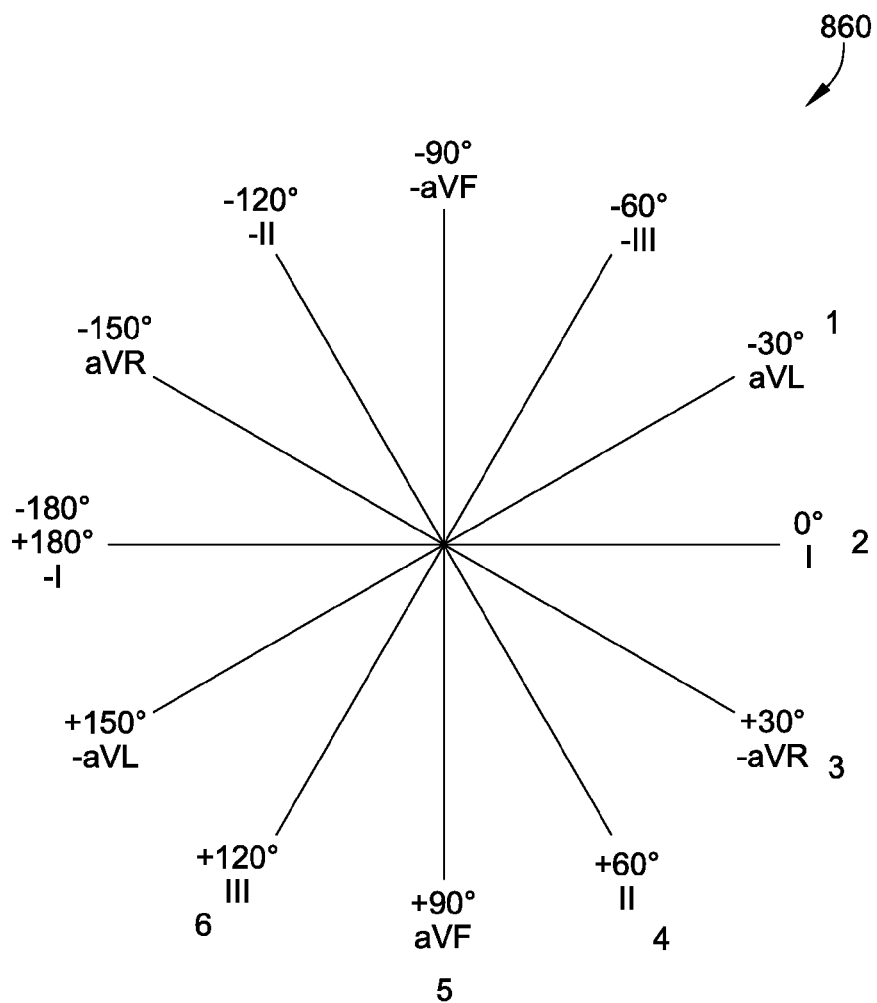
FIG. 8B shows the orientation plane of each lead of a set of electrodes adapted for monitoring an ECG signal and the order in which they are displayed on a display according to this disclosure.

The advantages from ordering the singular data points in accordance with the Cabrera sequence is seen in connection with FIG. 8B which depicts the vector orientation plane 860 of each of ECG leads I, II, III, aVR, aVL, aVF adapted for monitoring an ECG signal. These ECG leads are shown with the number 1 to 6 in FIG. 8C. As evident from FIG. 8C, the order in which the orientation planes of the ECG data are sequentially displayed on display 800 of FIG. 8A is sequentially from the 1) −30:+150 degree plane to the 2) 0:−180 degree plane to the 3) +30:-150 degree plane to the 4) +60:-120 degree plane to the 5) +90:-90 degree plane and finally to the 60 +120:-60 degree plane, before the ECG display starts this pattern all over again. Hence, by ordering the singular data points according to the Cabrera sequence according to this disclosure, a user is able to visualize the heart rhythm according to how the orientation plane of each ECG waveform from each lead of a set of ECG leads is occurring sequentially in space. Since the sequential orientation plane of each ECG waveform from each ECG lead simulates the signals that a user would see by walking around the heart, this disclosure advantageously allows a user to better visualize the spatial relationship of the singular data points taken from ECG waveforms in accordance with this disclosure with respect to the heart. This provides the user with additional information useful for interpreting the heart rhythm.

Display of the Cabrera ordered set of single data points is illustratively done using mapping techniques. As one example, FIG. 8C shows a table 870 illustrating data in a Cabrera structured ST-segment data set 874 for 12 ECG leads and the recurrent display slot order 875 for displaying this 12 ECG lead data on the display 800 of FIG. 8A according to this disclosure. Data order 872 is the same 1-12 numbering order appearing in data order 740 in FIG. 7B previously discussed. ECG lead order 873 is the same order of ECG leads as appearing in ECG lead order 750 in FIG. 7B and is shown only for comparison with the ordering of the data in the Cabrera structured ST-segment data set 874 and more particularly with the ordering of the ECG leads in the Cabrera sequence which are generating the data in the Cabrera structured ST-segment data set 874 of this disclosure. The Cabrera structured ST-segment data set 874 contains the singular ST-segment data point for ECG waveforms from each of the 12 ECG leads that are structured in the order in which those ECG waveforms would be presented in the Cabrera sequence. Recurrent display slot order 875 is used to associate the ST-segment data for each ECG waveform with one of the twelve display spaces or slots in which the display 800 in FIG. 8A has been divided in this example as described below.

As discussed in connection with FIG. 7A, large amounts of data representing each ECG waveform taken from 12 ECG leads requires the display domain to be divided into a twelve display spaces or slots arranged in a 3×4 matrix in order to display that data in a meaningful fashion on display 700. In this disclosure, as shown in FIG. 8A, the display 800 is divided into twelve display slots 855-865 arranged linearly across the screen. These display slots are organized in recurrent display slot order 875 as shown in FIG. 8C. As also shown in FIG. 8C each display slot is associated with one ST-segment data point in the Cabrera structured ST-segment data set 874. The sequential one of the display slots in the recurrent display slot order 875 ensure the sequential ordering of the each ST-segment data in the Cabrera structured data set to form a sequentially display domain ordered Cabrera structured data set on the display 800 of FIG. 8A. Each data in the sequentially display domain ordered Cabrera structured data set 874 is then displayed on the linear scale 801 of the display 800 in the order in which the data appears in the sequentially display domain ordered Cabrera structured data set.

FIG. 8C also shows a band of normal limits 876, labels 877, and anatomical areas 878 which may also be associated with the Cabrera structured ST-segment data set 874 and displayed with the data. While FIG. 8C shows the Cabrera structured ST-segment data set 874 as a Cabrera structured ST-segment data set, this disclosure covers the structuring of data in other ways. In addition, while the foregoing disclosure describes the display of all 12 data points taken from ECG waveforms generated by ECG leads of the 12 ECG standard, this disclosure provides for the display of fewer data or more data points. In addition, constellations of leads other than the 12 ECG standard may be used for generating the ECG waveforms from which the singular data points of this disclosure may be derived. Techniques for generating ECG waveforms other than ECG leads may also be used with the disclosure.

Referring again to FIG. 8A, the band of normal limits 830 is illustratively a predetermined range of high low values that may be typical for each of the data points in the spectrum of data that may make up an attribute. For example, FIG. 8A displays ST-segment information. As previously discussed, ST-segment information is a pattern of data that occurs along a certain part of an ECG waveform. The band of normal limits 830 shown in FIG. 8A may thus be the high low value that may be typical for each data point of the spectrum of data making up the ST-segment attribute. As seen in FIG. 8A, when displayed, the spectrum of high low data points typical for the attribute takes the form of a "continuous" band having an upper boundary and a lower boundary which extends across the length of the display.

While the illustrative example displays a range of high low values typical for each of a continuum of data points in the spectrum of data that make up an attribute, it will be appreciated that the range of high low values that form the band of normal limits may be taken from a subset of that continuum of data points that make up the attribute. For example, the subset may consist of a high low value typical for a patient for each of the one or more data points 810-821 in which case the band of normal limits 830 is the composite display of this set of typical high low values for each displayed data point. In the case were only one data point is displayed, the band of normal limits would be the high low value for the one displayed data point. In the case where the subset consists of a high low value typical for a patient for each of the one or more data points 810-812, each of the high low values for each of the two or more data points may further be interconnected in the manner described in connection waveform 808. More particularly, each of the adjacent high values associated with each data point may be interconnected to form an upper boundary of the band of normal limits. In addition, each of the adjacent low values associated with each data point may be interconnected to form a lower boundary of the band of normal limits. In this case, the upper and lower boundaries provide the user with a second order interpretation of the first order high low value data points similar to the second order interpretation provided by the waveform 808 to the first order singular data points as described in connection with waveform 808.

As shown in FIG. 8A, the band of normal limits 830 illustratively extends across the display 800. Hence, a user can readily see where the actual singular data point taken from an attribute of an ECG waveform taken from an ECG lead on a patient actually fits with respect to the typical high low value for that singular data point as depicted by the band of normal limits 830. In addition, a user can also readily see how the collection of singular data points displayed fits with respect to the composite high low range for each of the singular data points as represented by the band of normal limits 830. In addition, each singular data point may be changing over time. Hence, the band of normal limits enables a user to observe how any one or more singular data points or the entire collection of data points is comparing to a corresponding set of predetermined typical high low values over time. Information provided by the band of normal limits, including whether any one or more singular data points is falling outside of the high low value range typical for the associated attribute and if so, by how much, enables a user to better understand and diagnose the rhythm of the heart.

The predetermined range of normal values for the band of normal limits 830 is illustratively high low values derived from statistical data from a population of healthy patients. The range of values may also be based upon historical data of the patient that is having the ECG done. Other ways in which to define a range of normal values for the one or more data points displayed are known in the art and may be used under this disclosure. The band of normal limits 830 enables a user to quickly pinpoint regions of the heart that are displaying abnormal or irregular heart rhythm.

The band of normal limits 830 for the one or more data points may be adaptive based upon the historical data, etc. Hence, the band of normal limits may be treated as a variable that may be programmed by the user or automatically depending upon a variety of factors. For instance, the band of normal limits for use with a patient may be programmed based upon the sex of the patient, the age of the patient, the race of the patient, or on other criteria. In addition, the band of normal limits may be displayed in a color or a shade in order to better contrast the band of normal limits 830 from the one or more data points 810-821, which may also be displayed in a color for better visibility and/or contrast. In one example, the band of normal limits 830 is displayed in the color green in order to provide a better contrast with the data points which are illustratively displayed in the color blue. Alternatively, the band of normal limits and the one or more data points may be displayed using the same or set of colors different from the colors described above. In addition, shading, hatching, or other visual techniques may be used to provide contrast between the band of normal limits 830 and the one or more data points 810-821. Further, the techniques described to provide better contrast between the band of normal limits and the one or more data points may be used to provide better contrast between any of the other objects that may be displayed on the display 800 of FIG. 8A in order to allow for an easier read of the displayed information.

Anatomical area 840 is a label 840 for an anatomical area such as lateral, inferior, septal, anterior, lateral, and posterior areas of the heart that may be associated with and displayed with the one or more data points on the linear scale 801. The label may further associate the one or more data points to the left ventricle, or to the coronary arteries. The label may further associate the one or more data points to a STEMI criteria. The label may additionally associate the one or more data points to whether the one or more data points meet STEMI criteria. The anatomical area or labels associated with the one or more data points enables the user to readily know the anatomical area of the heart exhibiting an irregularity on account of the associated one or more of the one or more data points falling outside the band of normal limits. This enables more precise diagnosis of heart rhythms.

Figure 9:
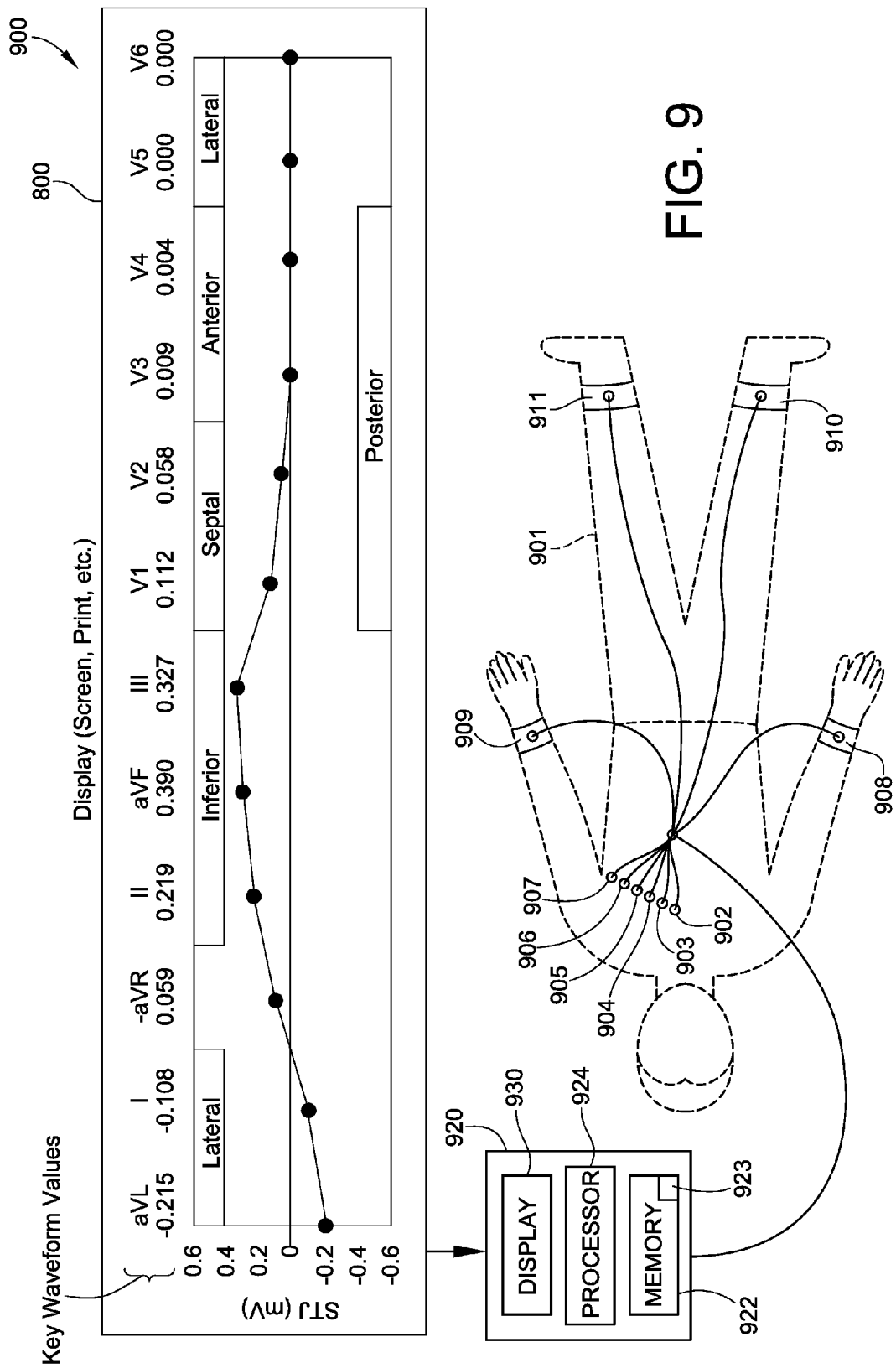
FIG. 9 shows a display of ECG data from a patient according to an illustrative system of this disclosure.

FIG. 9 shows an illustrative ECG monitoring system 900 for identifying ECG deviation data of a patient 901. The system 900 comprises: a set of electrodes 902-911 adapted for monitoring the ECG of a patient; a display 930; a processor 924 configured to control the display 930, a memory 922, an instance 923, and the display 800 of FIG. 8A. The memory 922, instance 922, processor 924, and display 930 may be integrated into a housing 920. Alternatively, these components may be provided separately. For example, the display 930 may be provided as a stand-alone monitor (not shown) that may be tethered or wirelessly connected to a computer (not shown) that includes the memory and processor shown in FIG. 9.

Processor 924 is configured to execute an instance for identifying ECG deviation of a patient. The processor 924 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Memory 922 may be implemented in any number of ways. Such ways include, by way of example and not of limitation, nonvolatile memories (NVM), read-only memories (ROM), random access memories (RAM), any combination of these, etc. Memory 922, if provided, may include programs containing instructions for execution by processor 924 or other processors that may be included in the external defibrillator. The programs provide instructions for execution by the processor 924.

The memory stores the instance 923 for identifying ECG deviation of a patient. The instance 923 for identifying ECG deviation of a patient are executable instructions stored in memory 922 for identifying ECG deviation of a patient from ECG waveforms generated by leads 902-911 and displaying the ECG deviation of the patient on the display 930. The instance 923 may include any one or combination of the methods for displaying ECG data of a patient on a display disclosed in this disclosure.

Display device 930 may be a visual display capable of displaying ECG waveform data. Displays for use with this disclosure may include an LCD screen, an e-paper display, or other bi-stable display, a CRT display or any other type of visual display. It may also include printers that print hard copy prints of ECG waveform data. Any device for presenting real or tangible displays of ECG waveform data are covered by this disclosure.

Display 830 is the display of the ECG deviation data of a patient as described in connection with FIG. 8A above on display device 930. In the case of the display of ECG deviation data on the display device 930, display 800 would be the tangible information appearing on the display device 930 during display of the ECG data. In the case of a display of ECG deviation data on a hard copy print-out, display 800 would be the hard the ECG deviation data displayed on the hard copy medium. The foregoing embodiments are examples only and any display of ECG deviation data in any format and on any medium is provided by this disclosure.

Figure 10:
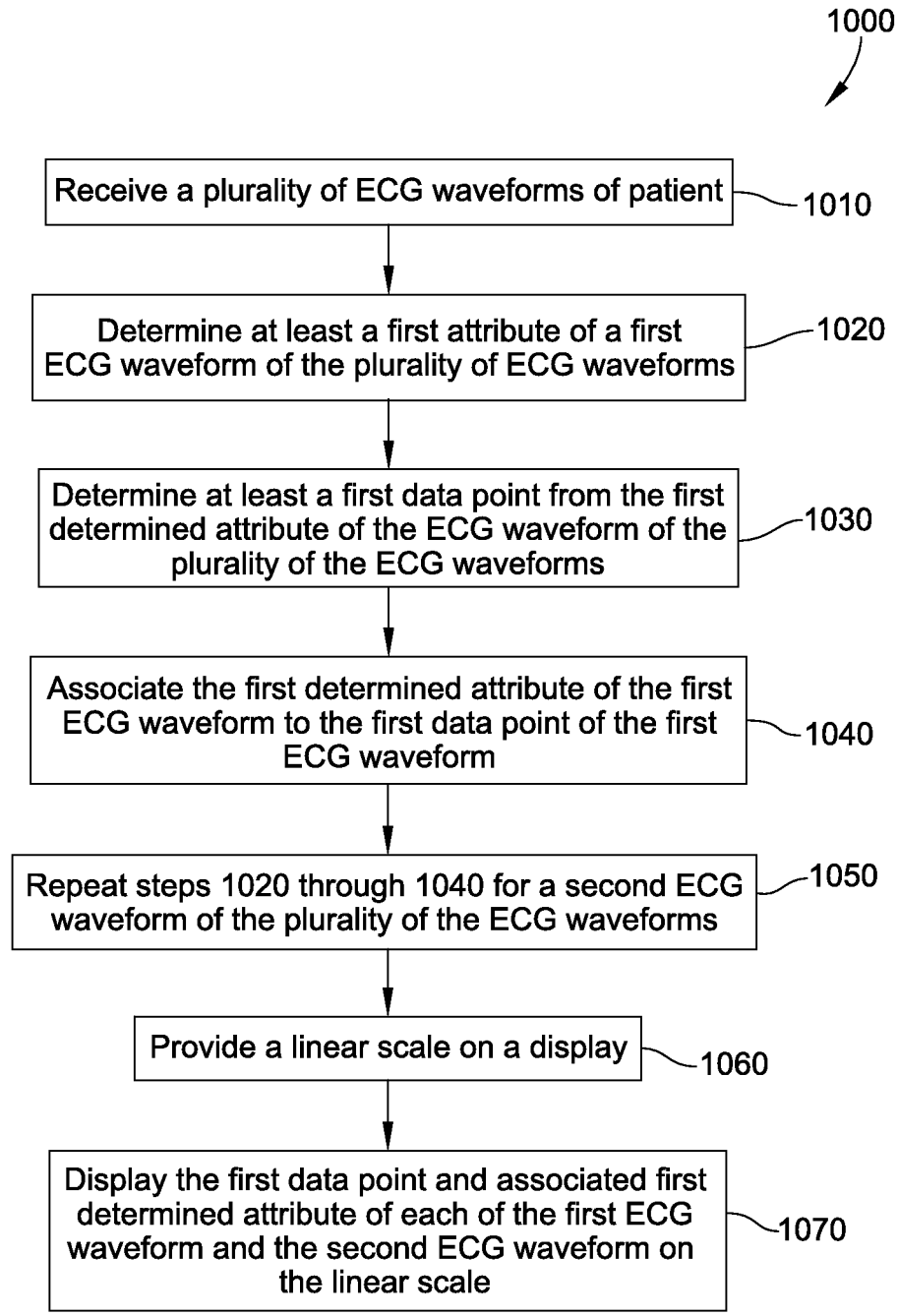
FIGS. 10, 11, 12 show illustrative methods for displaying ECG data from a patient according to this disclosure.

FIG. 10 shows an illustrative method 1000 for displaying ECG data of a patient according to this disclosure including the steps of: (a) receiving a plurality of ECG waveforms 1010 of a patient; (b) determining at least a first attribute 1020 of a first ECG waveform of the plurality of the ECG waveforms; (c) determining at least a first data point 1030 from the first attribute of the first ECG waveform of the plurality of the ECG waveforms; (d) associating 1040 the first determined attribute of the first ECG waveform to the first data point of the first ECG waveform; (e) repeating 1050 steps b through d for a second ECG waveform of the plurality of the ECG waveforms; (f) providing a linear scale 1060 on a display; and (g) displaying 1070 the first data point and associated first determined attribute of each of the first ECG waveform and the second ECG waveform on the linear scale.

The method may further include the step of: (h) associating anatomical area data to the at least one data point; and (i) displaying the anatomical area data on the linear scale. The anatomical area data may illustratively be taken from the group consisting of lateral, inferior, septal, anterior, lateral, and posterior anatomical areas. The at least a first data point may represent an ST level. The at least the first data point and the at least the first associated attribute may be displayed on the linear scale in accordance with the Cabrera sequence.

The illustrative method may further include the steps of: (h) associating a band of normal limits data to the at least one data point; and (i) displaying the band of normal limits data on the linear scale. The band of normal limits may be a variable taken from the group consisting of sex, age, and race of the patient.

The illustrative method may further include the step of: (h) associating a label with the at least one data point; (i) displaying the label for the at least one data point on the linear scale. The label may be configured to associate the at least one data point to one of a group consisting of the left ventricle, the coronary arteries, a STEMI criteria, and the condition of meeting the STEMI criteria.

Figure 11:
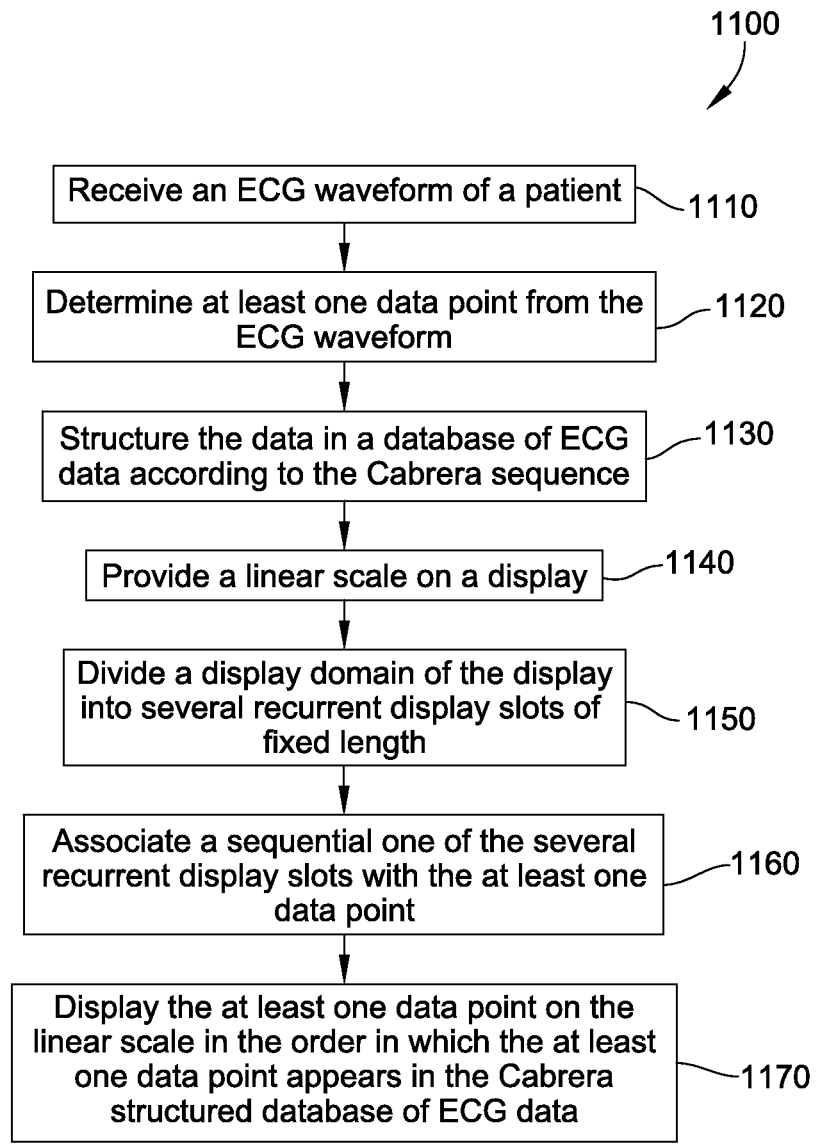

FIG. 11 shows an alternative method 1100 for displaying ECG data of a patient including the steps of: receiving an ECG waveform 1110 of a patient; determining at least one data point 1120 from the ECG waveform; structuring the data 1130 in a database of ECG data according to the Cabrera sequence; providing a linear scale 1140 on a display; dividing a display domain of the display 1150 into several recurrent display slots; associating 1160 a sequential one of the several recurrent display slots with the at least one data point; displaying 1170 the at least one data point on the linear scale in the order in which the at least one data point appears in the Cabrera structured database of ECG data. The at least one data point may be a plurality of data points and the method may further comprise the step of interconnecting the plurality of data points to form a waveform.

The step of displaying the at least one data point on the display may include the steps of: displaying the at least one data point along a horizontal axis of the display in the sequential order in which the at least one data point appears in the Cabrera structured database; and displaying the magnitude of the at least one data point in the sequential order in which the at least one data point appears in the Cabrera structured database along a vertical axis of the display. The at least one data point of a patient may be indicative of an ST segment of a patient and the magnitude for the at least one data point may be the ST-level for the ST segment. The at least the at least one data point in the Cabrera structured database may be stored in a table in a memory The method of claim may further include the steps of: associating a band of normal limits with the at least one data point in the Cabrera structured database; and displaying the band of normal limits for the at least one data point in the structured database on the display. The method may further include the steps of: associating a color of shade to the band of normal limits for the at least one data point in the Cabrera structured database; displaying the shade of the band of normal limits on the display. The method may further comprising the steps of associating a label with the at least one data point in the Cabrera structured database; and displaying the label with the at least one data point on the display.

The label associated with the at least one data point in the Cabrera structured database may associate the at least one data point to one of a group consisting of the left ventricle, the coronary arteries, a STEMI criteria, and whether the at least one data point in the Cabrera structured database meets STEMI criteria. The band of normal limits for the at least one data point in the Cabrera structured database associates may be a variable taken from the group consisting of the patient, the age of the patient, and the race of the patient.

Figure 12:
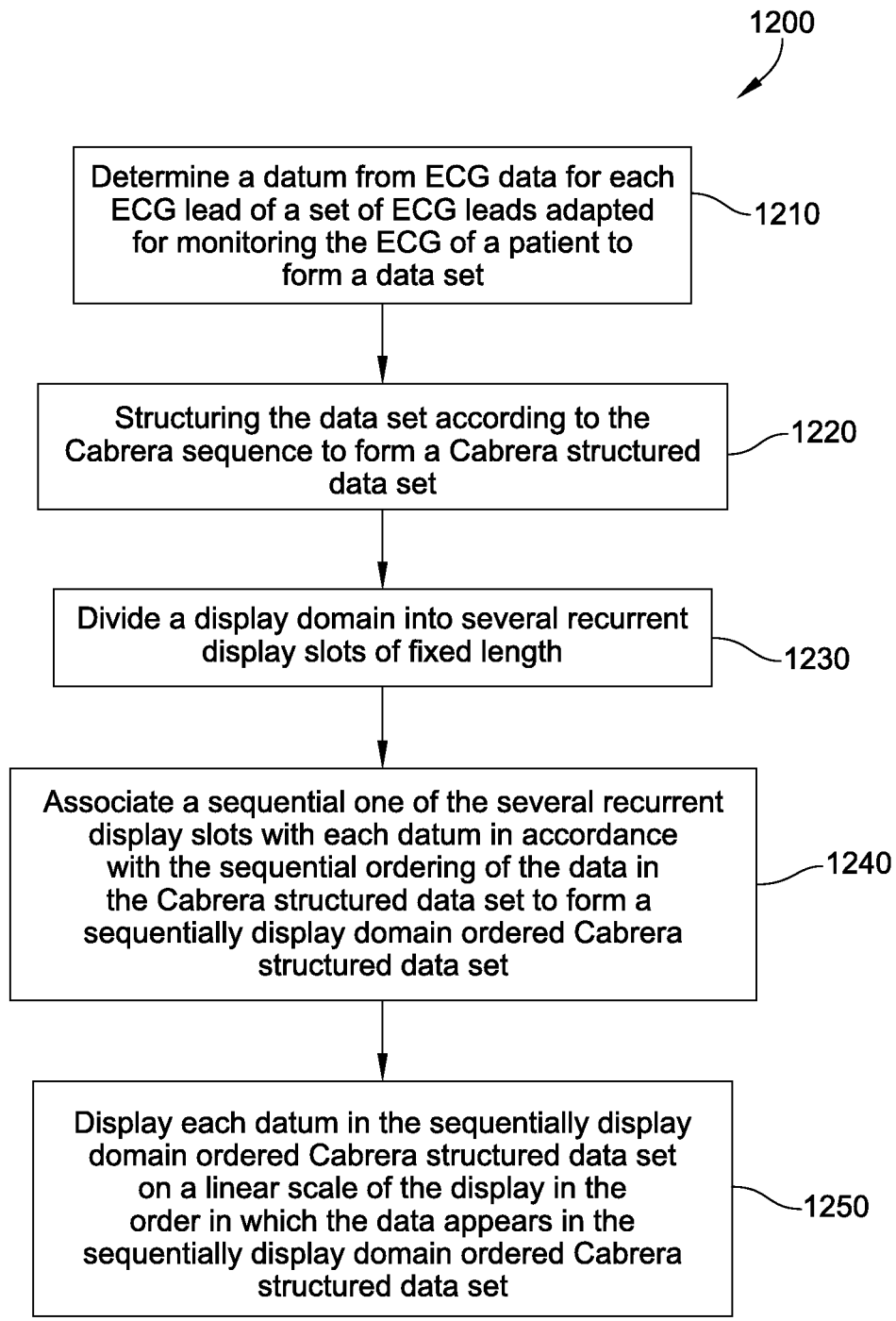

FIG. 12 shows an alternative method 1200 for displaying ECG data of a patient including the steps of: determining a data point 1210 from ECG data for each ECG lead of a set of ECG leads adapted for monitoring the ECG of a patient to form a data set; structuring the data set 1220 according to a predetermined sequence to form a structured data set; dividing a display domain 1230 into several recurrent display slots; associating 1240 a sequential one of the several recurrent display slots with each data in accordance with the sequential ordering of the each data in the structured data set to form a sequentially display domain ordered structured data set; displaying 1250 each data in the sequentially display domain ordered structured data set on a linear scale of the display in the order in which the data appears in the sequentially display domain ordered structured data set.

The method may further include the step of associating an attribute of the ECG waveform to the data for the each ECG lead of the set of ECG leads. The data of a patient may be a data indicative of an ST segment of a patient. The step of displaying on a linear scale of the display each data in the sequentially display domain ordered Cabrera structured data set may include the steps of: displaying each data along a horizontal axis of the display in the sequential order in which the data appears in the sequentially display domain ordered Cabrera structured data set; and displaying a -magnitude for each data in the sequentially display domain ordered Cabrera structured data set along a vertical axis of the display. The data of a patient may be data indicative of an ST segment of a patient and the magnitude for each data may be the ST-level for the ST segment. The sequentially display domain ordered Cabrera structured data set may be stored in a table in a memory. The data for each ECG lead of the set of ECG leads may be associated with a band of normal limits. The method may further include the steps of: associating a color of shade to the band of normal limits for the at least one data point in the Cabrera structured database; and displaying the shade of the band with the band of normal limits on the display.

The data for each ECG lead of the set of ECG leads may be associated with a label. The label associated with the one or more of the data in the sequentially display domain ordered Cabrera structured data set may associate the one or more of the one or more of the in the sequentially display domain ordered Cabrera structured data set to one of a group consisting of: the left ventricle, the coronary arteries; a STEMI criteria; and a STEMI criteria. The band of normal limits for the each data in the sequentially display domain ordered Cabrera structured data set on the display may be a variable taken from the group consisting of: the sex of the patient, the age of the patient, and the race of the patient.

There is thus seen a disclosure of first order interpreted singular data points for an attribute 807 taken from one or more ECG waveforms generated by one or more ECG leads. The first order interpreted singular data are easy to read and are cleanly presented on a linear axis. There is also seen a second order interpretation of a collection of first order interpreted singular data points provided in the form of waveform 808 that enables a user to understand how the collection of first order interpreted singular data points are changing as a group over time. In addition, the presentation of these singular data points according to the Cabrera sequence presents the first order singular data points 810-821 and waveform 808 in the sequential order of the orientation plane of each ECG waveform from each ECG lead. This allows the user to better visualize the relationship of those signals with respect to the heart. Further, the band of normal limits provides an easy to read gauge that allows the user to readily determine whether any one or more singular data points of the one or more data points falls within or outside of the typical range depicted by the band of normal limits. Moreover, the anatomical area associated with the one or more data points brings further information, such as the anatomical area origin of each of the one or more data points which gives the user a better understanding of the relationship of each of the one or more data points to the heart. The association of labels with the one or more data points may provide the user with even further information useful in understanding the heart rhythm. These and other features of this disclosure provide for a display of ECG data to a user that is simple, easy in presentation, easy to understand, easy to use, quickly communicates critical information including first order data point interpretation provided by singular data points and second order interpretation provided by a waveform of transformative first order data, enables the user to better visualize the orientation plane of the different ECG data with respect to the heart, is user friendly, intuitive, and enables the user to efficiently and effectively interpret and diagnose the heart rhythm of a patient.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense.

Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

We claim:

1. A method for displaying ECG data of a patient, the method comprising:
   a. determining, in a manner other than deviation from a patient-specific baseline, a singular data point that represents a time-domain value of the ECG data for each ECG lead of a set of ECG leads adapted for monitoring the ECG of a patient to form a data set;
   b. structuring the data set according to a Cabrera sequence that includes both limb leads and chest leads, to form a Cabrera structured data set;
   c. defining a horizontal row of several recurrent display slots in a display domain of a display, the several recurrent display slots including at least one display slot for each limb lead and each chest lead, ordered in the horizontal row according to the Cabrera sequence;
   d. associating a sequential one of the several recurrent display slots with each singular data point in accordance with the sequential ordering of the each singular data point in the Cabrera structured data set to form a sequentially display domain ordered Cabrera structured data set;
   e. displaying each singular data point in the sequentially display domain ordered Cabrera structured data set on a linear scale of the display in the order in which the data appears in the sequentially display domain ordered Cabrera structured data set as the only ECG data displayed at a time on the linear scale; and
   f. displaying each singular data point associated with each of the several recurrent display slots with interconnections between the displayed data points to form a single waveform across all of the recurrent display slots.

2. The method of claim 1 wherein the ECG data of a patient is data indicative of an ST segment of a patient and a magnitude for each singular data point is an ST-level for the ST segment.

3. The method of claim 1 further comprising the step of:
   g. associating an attribute of an ECG waveform to the singular data point for each ECG lead of the set of ECG leads.

4. The method of claim 3 wherein the singular data point for each ECG lead of the set of ECG leads is indicative of an ST segment of a patient.

5. The method of claim 1 wherein the singular data point for each ECG lead of the set of ECG leads is associated with a band of normal limits.

6. The method of claim 5 further comprising the steps of:
   g. associating a color of shade to the band of normal limits for the at least one data point in the Cabrera structured data set;
   h. displaying the shade of the band with the band of normal limits on the display.

7. The method of claim 5 wherein the band of normal limits for the each singular data point in the sequentially display domain ordered Cabrera structured data set on the display depends on a parameter selected from the group consisting of: the sex of the patient, the age of the patient, and the race of the patient.

8. The method of claim 1 wherein the singular data point for each ECG lead of the set of ECG leads is associated with a label.

9. The method of claim 8 wherein the label associated with each singular data point in the sequentially display domain ordered Cabrera structured data set is one of a group consisting of: the left ventricle, the coronary arteries; and a STEMI criteria.

10. The method of claim 1 wherein the step of displaying comprises the steps of:
    e(i) displaying each singular data point along a horizontal axis of the display in the sequential order in which the data appears in the sequentially display domain ordered Cabrera structured data set; and
    e(ii) displaying a magnitude for each singular data point in the sequentially display domain ordered Cabrera structured data set along a vertical axis of the display.

11. The method of claim 1 wherein the sequentially display domain ordered Cabrera structured data set is stored in a table in a memory.

12. A method for displaying ECG data of a patient, the method comprising:
    a. receiving an ECG waveform of a patient;
    b. determining at least one data point representing only a portion of the ECG waveform from a time domain portion of the ECG waveform in a manner other than deviation from a patient-specific baseline;
    c. structuring the data in a database of ECG data according to a Cabrera sequence that includes both limb leads and chest leads;
    d. providing a linear scale on a display;
    e. defining a horizontal row of several recurrent display slots in a display domain of the display, the several recurrent display slots including at least one display slot for each limb lead and each chest lead, ordered in the horizontal row according to the Cabrera sequence;
    f. associating a sequential one of the several recurrent display slots with the at least one data point based on the order in which the at least one data point is stored in the Cabrera structured database of ECG data;
    g. displaying the at least one data point on the linear scale in the sequential one of the several recurrent display slots associated with the at least one data point as the only ECG data displayed at a time in the sequential one of the several recurrent display slots; and
    h. displaying the data points associated with each of the several recurrent display slots with interconnections between the displayed data points to form a single waveform across all of the recurrent display slots.

13. The method of claim 12 wherein the at least one data point of a patient is indicative of an ST segment of a patient and a magnitude for the at least one data point is an ST-level for the ST segment.

14. The method of claim 12 further comprising the steps of:
    h. associating a band of normal limits with the at least one data point; and
    i. displaying the band of normal limits for the at least one data point on the display.

15. The method of claim 14 further comprising the step of:
    j. associating a color of shade to the band of normal limits for the at least one data point in the Cabrera structured database;
    k. displaying the shade of the band with the band of normal limits on the display.

16. The method of claim 14 wherein the band of normal limits depends on a parameter selected from the group consisting of: the sex of the patient, the age of the patient, and the race of the patient.

17. The method of claim 14 further comprising the step of:
l. associating a label with the at least one data point; and
m. displaying the label with the at least one data point on the display.

18. The method of claim 17 wherein the label associated with the at least one data point in the Cabrera structured database associates the at least one data point to one of a group consisting of the left ventricle, the coronary arteries, a STEMI criteria, and an indication that the at least one data point in the Cabrera structured database meets STEMI criteria.

19. The method of claim 12 wherein the step of displaying the at least one data point comprises the steps of:
g(i) displaying the at least one data point along a horizontal axis of the display in the sequential order in which the at least one data point appears in the Cabrera structured database; and
g(ii) displaying a magnitude of the at least one data point in the sequential order in which the at least one data point appears in the Cabrera structured database along a vertical axis of the display.

20. The method of claim 12 wherein the Cabrera structured database is stored in a table in a memory.

21. An ECG monitoring system for identifying ECG deviation data of a patient, the system comprising:
a set of leads adapted to monitor the ECG of a patient;
a display;
a processor configured to control the display and to execute an instance that during execution is operative to:
determine, in a manner other than deviation from a patient-specific baseline, a singular data point that represents a time-domain value of the ECG data for each ECG lead of the set of ECG leads adapted for monitoring the ECG of a patient to form a data set;
structure the data set according to a Cabrera sequence that includes both limb leads and chest leads, to form a Cabrera structured data set;
define a horizontal row of several recurrent display slots in a display domain, the several recurrent display slots including at least one display slot for each limb lead and each chest lead, ordered in the horizontal row according to the Cabrera sequence;
associate a sequential one of the several recurrent display slots with each singular data point in accordance with the sequential ordering of the each singular data point in the Cabrera structured data set to form a sequentially display domain ordered Cabrera structured data set;
render each singular data point in the sequentially display domain ordered Cabrera structured data set on a linear scale of a display in the order in which the singular data point appears in the sequentially display domain ordered Cabrera structured data set as the only ECG data displayed at a time on the linear scale; and
display each singular data point associated with each of the several recurrent display slots with interconnections between the displayed data points to form a single waveform across all of the recurrent display slots.

22. The ECG monitoring system of claim 21 wherein the singular data point for each ECG lead of the set of ECG leads is indicative of an ST segment of a patient.

23. The ECG monitoring system of claim 21, the instance further operative to:
associate an attribute of an ECG waveform to the singular data point for each ECG lead of the set of ECG leads;
render the attribute on the linear scale.

24. The ECG monitoring system of claim 23, the instance further:
associating a band of normal limits data to the singular data point for each ECG lead of the set of ECG leads;
displaying the band of normal limits data on the linear scale.

25. The ECG monitoring system of claim 23, the instance further operative to:
associate anatomical area data to the singular data point for each ECG lead of the set of ECG leads;
render the anatomical area data on the linear scale.

* * * * *